US010942176B2

(12) United States Patent
Healy et al.

(10) Patent No.: US 10,942,176 B2
(45) Date of Patent: Mar. 9, 2021

(54) ANTIGEN DETECTION USING PHOTOCLEAVABLE LABELS

(71) Applicant: AGILENT TECHNOLOGIES, INC., Santa Clara, CA (US)

(72) Inventors: Mimi Healy, Houston, TX (US); Xiyi Chen, Houston, TX (US); Jinchun Wang, Houston, TX (US); Weidong Wu, Houston, TX (US); Sophia Petrichenko, Houston, TX (US); Su Zhang, Houston, TX (US); Stacie Frye, Houston, TX (US)

(73) Assignee: Agilent Technologies, Inc., Santa Clara, CA (US)

(*) Notice: Subject to any disclaimer, the term of this patent is extended or adjusted under 35 U.S.C. 154(b) by 137 days.

(21) Appl. No.: 15/230,876

(22) Filed: Aug. 8, 2016

(65) Prior Publication Data
US 2017/0052175 A1 Feb. 23, 2017

Related U.S. Application Data

(60) Provisional application No. 62/201,978, filed on Aug. 6, 2015.

(51) Int. Cl.
G01N 33/543 (2006.01)
G01N 33/53 (2006.01)
G01N 33/58 (2006.01)
G01N 33/533 (2006.01)
B01L 3/00 (2006.01)
G01N 1/30 (2006.01)
G01N 1/31 (2006.01)
G01N 35/00 (2006.01)

(52) U.S. Cl.
CPC ........ *G01N 33/54306* (2013.01); *B01L 3/502* (2013.01); *G01N 1/30* (2013.01); *G01N 1/312* (2013.01); *G01N 33/533* (2013.01); *G01N 33/5308* (2013.01); *G01N 33/582* (2013.01); *G01N 35/00029* (2013.01); *B01L 2200/026* (2013.01); *B01L 2300/0627* (2013.01); *B01L 2400/082* (2013.01); *G01N 2001/302* (2013.01); *G01N 2035/00138* (2013.01)

(58) Field of Classification Search
CPC ....... B01L 2200/026; B01L 2300/0627; B01L 2400/082; B01L 3/502; G01N 1/30; G01N 1/312; G01N 2001/302; G01N 2035/00138; G01N 33/5308; G01N 33/533; G01N 33/54306; G01N 33/582; G01N 35/00029
See application file for complete search history.

(56) References Cited

U.S. PATENT DOCUMENTS

| | | | |
|---|---|---|---|
| 7,195,874 B2 | 3/2007 | Rothschild et al. | |
| 7,211,394 B2 | 5/2007 | Rothschild et al. | |
| 8,148,503 B2 | 4/2012 | Litosh et al. | |
| 9,383,371 B2 | 7/2016 | Lee et al. | |
| 10,041,115 B2* | 8/2018 | Stupi ................... | C07H 19/073 |
| 2005/0017191 A1 | 1/2005 | Montagu et al. | |
| 2008/0299637 A1 | 12/2008 | Gee et al. | |
| 2009/0203023 A1 | 8/2009 | Johnson | |
| 2011/0311966 A1* | 12/2011 | Hennig ................ | C12Q 1/6804 435/6.1 |
| 2013/0122489 A1* | 5/2013 | Stupi ................... | C07H 19/073 435/6.1 |
| 2014/0120532 A1* | 5/2014 | Lee ...................... | G01N 33/574 435/6.11 |

FOREIGN PATENT DOCUMENTS

| | | |
|---|---|---|
| CA | 2992492 | 1/1917 |
| CA | 2940764 | 9/2015 |
| CN | 2444230 | 8/2001 |
| CN | 101203596 | 6/2008 |
| CN | 101330931 A | 12/2008 |
| CN | 102230895 | 11/2011 |
| EP | 2728359 | 5/2014 |
| JP | 2009-538629 | 11/2009 |
| JP | 2011-518320 | 6/2011 |
| JP | 2014-532043 | 12/2014 |
| WO | WO 2006/116037 | 11/2006 |
| WO | WO 2007/140371 | 12/2007 |
| WO | WO 2009/124099 | 10/2009 |
| WO | WO 2013/040257 | 3/2013 |

OTHER PUBLICATIONS

Ramos et al., "Photocleavage of peptides and oligodeoxynucleotides carrying 2-nitrobenzyl groups," Helv. Chim. Acta, 2009, vol. 92, pp. 613-622.*
Chen et al., "Double staining immunohistochemistry," N. Am. J. Med. Sci., 2010, vol. 2, No. 5, pp. 241-245.*
Agasti et al., "Photocleavable DNA Barcode—Antibody Conjugates Allow Sensitive and Multiplexed Protein Analysis in Single Cells," J. Am. Chem. Soc., 134:18499-18502, 2012.
Aoki et al., "Design and synthesis of a photocleavable biotin-linker for the photoisolation of ligand-receptor complexes based on the photolysis of 8-quinolinyl sulfonates in aqueous solution," Bioord. Med. Chem., 17:3405-13, 2009.
Bai et al., "Design and synthesis of a photocleavable biotinylated nucleotide for DNA analysis by mass spectrometry," Nuc. Acids Res., 32:535-41, 2004.

(Continued)

Primary Examiner — Galina M. Yakovleva

(57) ABSTRACT

Provided herein are methods of using photocleavable labels for multiplex and serial antigen detection. The methods comprise detecting the presence of photocleavable labels, which are conjugated through functional linkers to antigen-binding complexes, which in turn non-covalently bind to antigens. The presence of a photocleavable label is indicative of the presence of an antigen specifically or selectively bound by an antigen-binding complex. Also provided are apparatuses for using photocleavable labels for multiplex and serial antigen detection.

17 Claims, 25 Drawing Sheets

Specification includes a Sequence Listing.

(56) References Cited

OTHER PUBLICATIONS

Deng et al., "An integrated microfluidic chip system for single-cell secretion profiling of rare circulating tumor cells," *Scientific Reports*, 4:7499, 2014.

Huang et al., "A biotin label-based antibody array for high-content profiling of protein expression," *Cancer Genomics Proteomics*, 7:129-41, 2010.

Olejnik et al., "Photocleavable biotin derivatives: a versatile approach for the isolation of biomolecules," *Proc. Natl. Acad. Sci. USA*, 92:7590-4, 1995.

PCT International Search Report and Written Opinion issued in International Application No. PCT/US2016-045981, dated Oct. 21, 2016.

Ullal et al., "Cancer Cell Profiling by Barcoding Allows Multiplexed Protein Analysis in Fine-Needle Aspirates," *Sci. Transl. Med.*, 6:219ra9, 2014.

Valley et al., "Sequential superresolution imaging of multiple targets using a single fluorophore," *PLoS ONE*, 10(4):E0123941, 2015.

Wirkner et al., "Triggered cell release from materials using bioadhesive photocleavable linkers," *Adv. Mater.*, 23: 3907-10, 2011.

Prichard et al., "Overview of Automated Immunohistochemistry," *Arch. Pathol. Lab. Med.*, 138:1578-1582, 2014.

Voigt et al., "Automated Indirect Immunofluorescence Evaluation of Antinuclear Autoantibodies on HEp-2 Cells", *Clin. Dev. Immunol.*, 2012:651058, 2012.

* cited by examiner

5'-/5Biotin/CGTACCCGCTTGGTCTTTCTCCCGTACCCCGCTTGGTCTTTCTCCCTGCCCCGGGTTCCTTCATTCTCT-dC-2-NB-Cy5
3'-GACGGGGCCCAAGGAGTAAGAGAGTACGAGGCAT/5Biotin/

FIG. 2

```
                                              dC-2-NB-Cy5 ☆
R  Red     /5Biotin/TACGCTGCCGGTGTCCTCATTCTCTCACTCGCTC dG-2-NB-AF594 ☆
O  Orange  /5Biotin/TACGCTGCCGGTGTCCTCATTCTCTCACTCGCTC dU-2-NB-AF532 ☆
G  Green   /5Biotin/TACGCTGCCGGTGTCCTCATTCTCTCACTCGCTC dA-2-NB-AF488 ☆
B  Blue    /5Biotin/TACGCTGCCGGTGTCCTCATTCTCTCACTCGCTC
```

*FIG. 4*

```
                                              dC-2-NB-Cy5 ☆
RR  Red    /5Biotin/TACGCTGCCGGTGTCCTCATTCTCTCACTCGCTC
                 GACGGCCACAGGAGTAAGAGAGTGAGCGAGGCAT/5Biotin/
         dC-2-NB-Cy5 ☆
                                              dG-2-NB-AF594 ☆
OO  Orange /5Biotin/TACGCTGCCGGTGTCCTCATTCTCTCACTCGCTCC
                 CGACGGCCACAGGAGTAAGAGAGTGAGCGAGGCAT/5Biotin/
         dG-2-NB-AF594 ☆
                                              dU-2-NB-AF532 ☆
GG  Green  /5Biotin/TACGCTGCCGGTGTCCTCATTCTCTCACTCGCTCCG
                 GCGACGGCCACAGGAGTAAGAGAGTGAGCGAGGCAT/5Biotin/
         dU-2-NB-AF532 ☆
                                              dA-2-NB-AF488 ☆
BB  Blue   /5Biotin/TACGCTGCCGGTGTCCTCATTCTCTCACTCGCTCCGT
                 TGCGACGGCCACAGGAGTAAGAGAGTGAGCGAGGCAT/5Biotin/
         dA-2-NB-AF488 ☆
```

*FIG. 5*

R Red        /5Biotin/TACGCTGCCGGTGTCCTCATTCTCTCACTCGCTC$^T$ $^T$ $^T$
                     GACGGCCACAGGAGTAAGAGAGTGAGCGAG$_T$ $_T$ $_T$
             dC-2-NB-Cy5 ☆

O Orange     /5Biotin/TACGCTGCCGGTGTCCTCATTCTCTCACTCGCTC$^T$ $^T$ $^T$
                     CGACGGCCACAGGAGTAAGAGAGTGAGCGAG$_T$ $_T$ $_T$
             dG-2-NB-AF594 ☆

G Green      /5Biotin/TACGCTGCCGGTGTCCTCATTCTCTCACTCGCTC$^T$ $^T$ $^T$
                     GCGACGGCCACAGGAGTAAGAGAGTGAGCGAG$_T$ $_T$ $_T$
             dU-2-NB-AF532 ☆

B Blue       /5Biotin/TACGCTGCCGGTGTCCTCATTCTCTCACTCGCTC$^T$ $^T$ $^T$
                     TGCGACGGCCACAGGAGTAAGAGAGTGAGCGAG$_T$ $_T$ $_T$
             dA-2-NB-AF488 ☆

FIG. 6

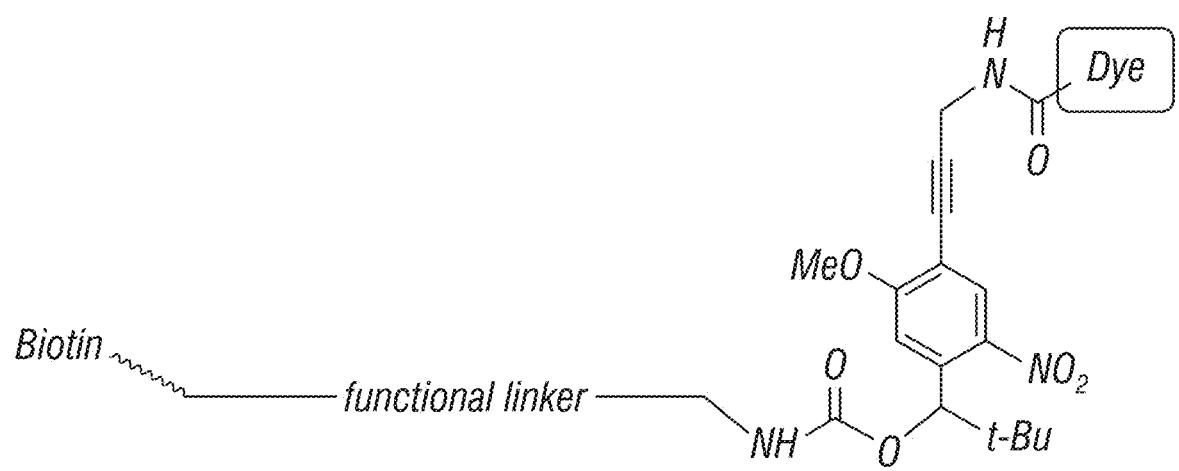

FIG. 7

*Before Cleavage* *After Cleavage*
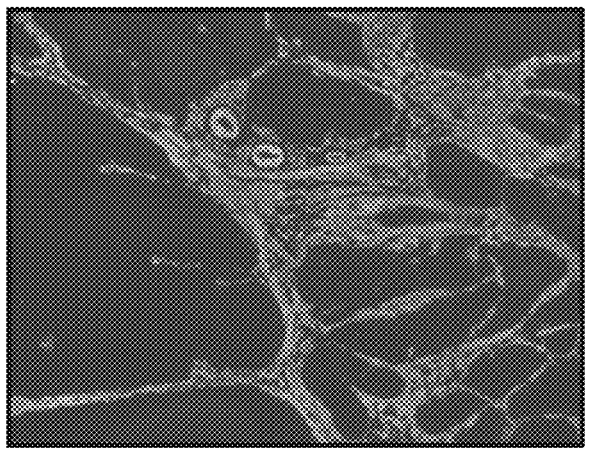 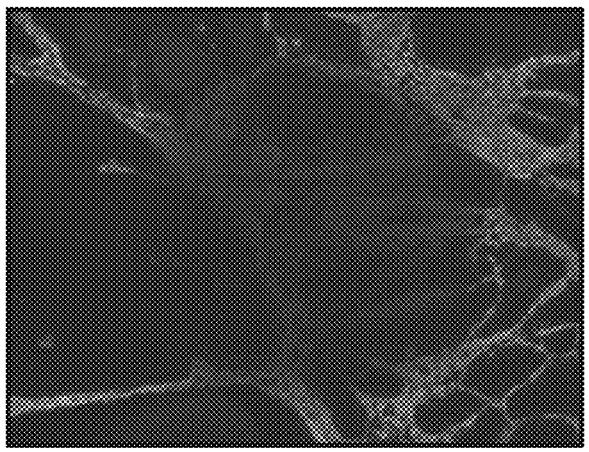
FIG. 10D
*Before Cleavage* *After Cleavage*
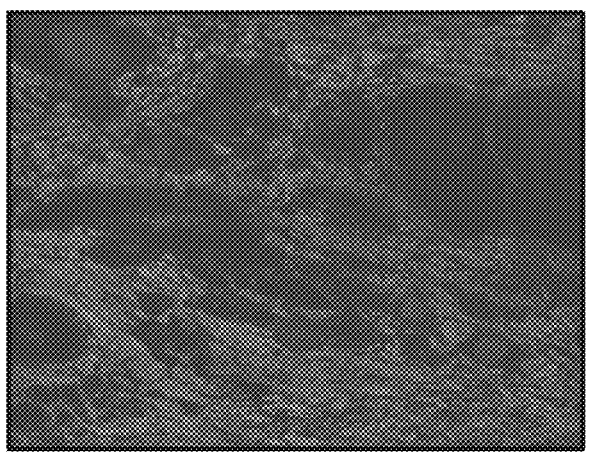 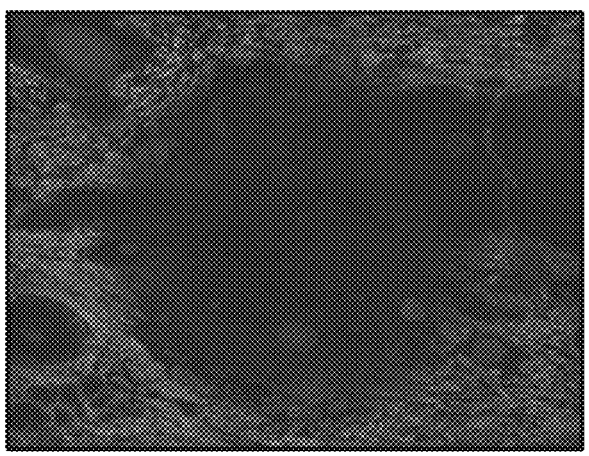
FIG. 10E

Before Cleavage        After Cleavage
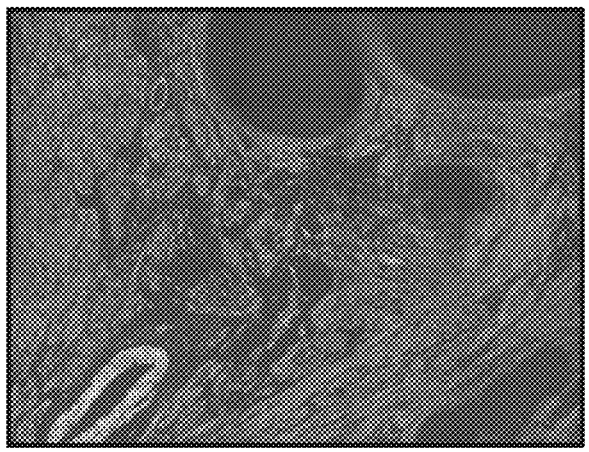 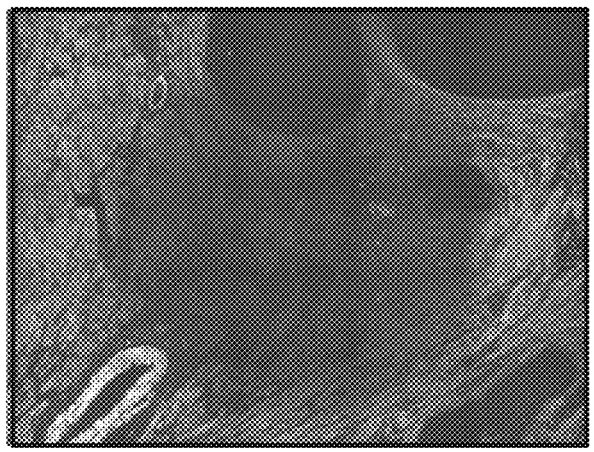
FIG. 10F
Before Cleavage        After Cleavage
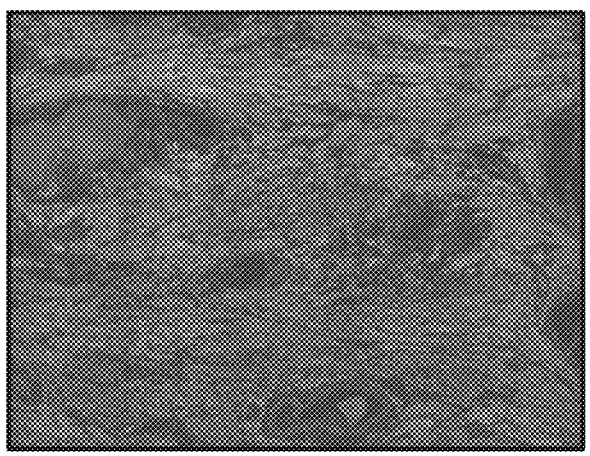 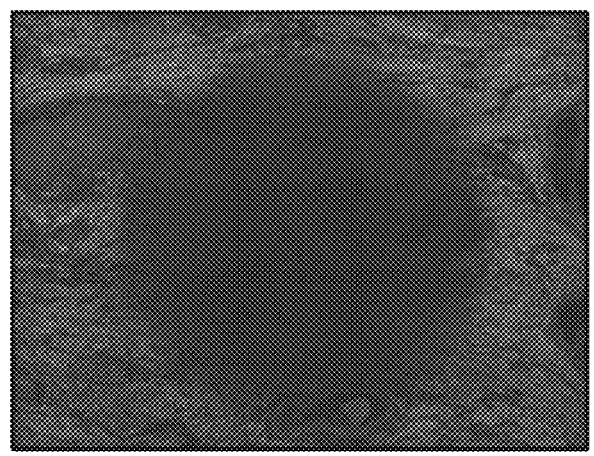
FIG. 10G

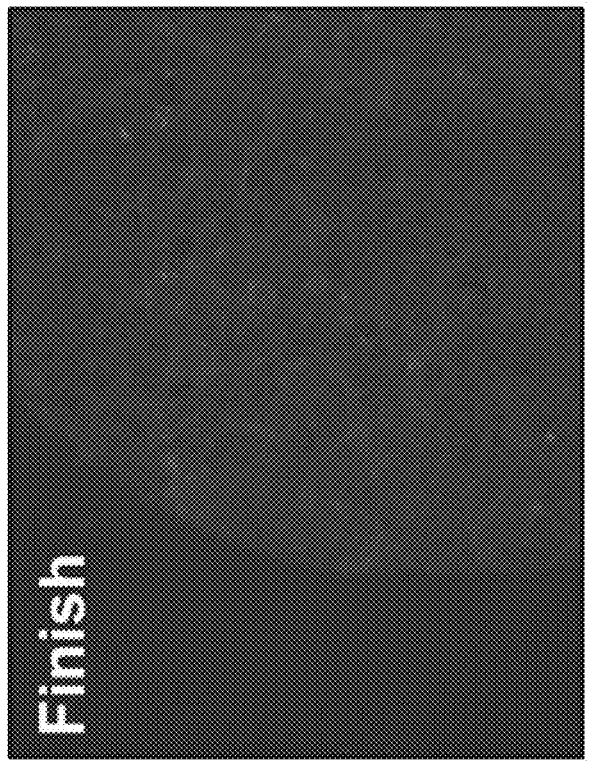
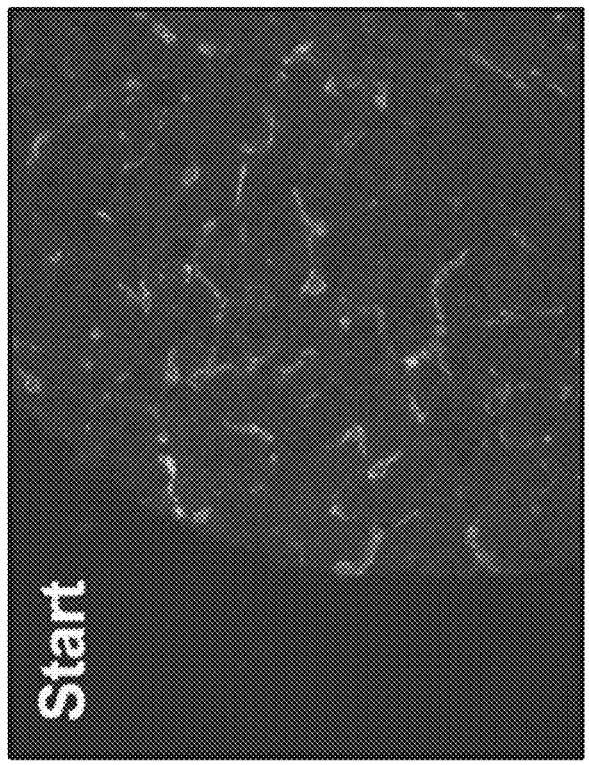
FIG. 21A

SEQUENCE LISTING

<160> NUMBER OF SEQ ID NOS: 17

<210> SEQ ID NO 1
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 1 cgtacccgc ttggtctttc tcccgtaccc cgcttggtct ttctccctgc cccgggttcc     60
tcattctctc                                                          70

<210> SEQ ID NO 2
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 2
tacggagcat gagagaatga ggaacccggg gcag                                   34

<210> SEQ ID NO 3
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 3
tacgctgccg gtgtcctcat tctctcactc gctc                                   34

<210> SEQ ID NO 4
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 4
tacggagcga gtgagagaat gaggacaccg gcag                                   34

<210> SEQ ID NO 5
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 5
tacgctgccg gtgtcctcat tctctcactc gctcc                                  35

<210> SEQ ID NO 6
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 6
tacggagcga gtgagagaat gaggacaccg gcagc                                  35

<210> SEQ ID NO 7
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 7
tacgctgccg gtgtcctcat tctctcactc gctccg                                 36

<210> SEQ ID NO 8
<211> LENGTH: 36
<212> TYPE: DNA
<213> ORGANISM: Artificial Sequence
<220> FEATURE:
<223> OTHER INFORMATION: Synthetic polynucleotide

```
<400> SEQUENCE: 8
tacggagcga gtgagagaat gaggacaccg gcagcg                                36

<210> SEQ ID NO 9
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 9
tacgctgccg gtgtcctcat tctctcactc gctccgt                               37

<210> SEQ ID NO 10
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 10
tacggagcga gtgagagaat gaggacaccg gcagcgt                               37

<210> SEQ ID NO 11
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 11
tacgctgccg gtgtcctcat tctctcactc gctctttttt gagcgagtga gagaatgagg      60
acaccggcag                                                             70

<210> SEQ ID NO 12
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 12
tacgctgccg gtgtcctcat tctctcactc gctctttttt gagcgagtga gagaatgagg      60
acaccggcag c                                                           71

<210> SEQ ID NO 13
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 13
tacgctgccg gtgtcctcat tctctcactc gctctttttt gagcgagtga gagaatgagg      60
acaccggcag cg                                                          72

<210> SEQ ID NO 14
<211> LENGTH: 73
<212> TYPE: DNA
<213> ORGANISM: Artificial Sequence
<220> FEATURE:
<223> OTHER INFORMATION: Synthetic polynucleotide

<400> SEQUENCE: 14
```

```
tacgctgccg gtgtcctcat tctctcactc gctctttttt gagcgagtga gagaatgagg      60
acaccggcag cgt                                                         73

<210> SEQ ID NO 15
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 15 agtacccgc ttggtctttc tcccgtaccc cgcttggtct ttctccctgc cccgggttcc      60
tcattctct                                                              69

<210> SEQ ID NO 16
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 16
agagagaatg aggaacccgg ggcagggaga aagaccaagc ggggtacggg agaaagacca     60
agcggggta                                                              69

<210> SEQ ID NO 17
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 17
ggacaccggc ag                                                          12
```

ANTIGEN DETECTION USING PHOTOCLEAVABLE LABELS

The present application claims the priority benefit of U.S. provisional application No. 62/201,978, filed Aug. 6, 2015, the entire contents of which is incorporated herein by reference.

BACKGROUND OF THE INVENTION

1. Field of the Invention

The present invention relates generally to the fields of histology, pathology, and molecular biology. More particularly, it concerns the use of photocleavable labels (PCLs) for antigen detection, including, for example, for multiplex and serial antigen detection.

2. Description of Related Art

In typically used immunostaining protocols, an antigen-specific antibody is added to an antigen-containing specimen including, but not limited to, a tissue section, a cell, or a protein blot, and allowed to bind to the antigen. This antigen bound antibody is then detected using any of a variety of techniques, including (a) a second antibody, with specific affinity for the first antibody, conjugated to a fluorophore (e.g., Cy5) or an enzyme used for colorimetric detection (e.g., HRP); (b) a second antibody, with specific affinity for the first antibody, conjugated to biotin which is subsequently detected using avidin or streptavidin conjugated to a fluorophore (e.g., Cy5) or an enzyme used for colorimetric detection (e.g., HRP); and (c) a fluorophore (e.g., Cy5) or an enzyme used for colorimetric detection (e.g., HRP) or biotin that is directly conjugated to the first antibody. In instance (a) and (b), such technologies allow for about three antibodies, each uniquely labeled, to be used on the same sample. In instance (c), such technologies are limited to about four antibodies conjugated to distinct labels that can be separately imaged. However, non-specific interactions between the secondary antibodies and the limited ability to detect individual labels prevent higher order multiplexing. New multiplex technologies are emerging, but many suffer drawbacks, e.g., time consuming, expensive, and/or require extensively optimized primary antibodies. Improved methods and instruments for automating antigen detection are desirable.

SUMMARY OF THE INVENTION

Provided herein are methods of using photocleavable labels for multiplex and serial antigen detection. The methods comprise detecting the presence of photocleavable labels, which are conjugated through functional linkers to antigen-binding complexes, which are in turn non-covalently bound to antigens. Thus, the presence of a photocleavable label is indicative of the presence of an antigen specifically or selectively bound by an antigen-binding complex.

In one aspect, methods are provided for detecting the presence of at least a first antigen on or in a sample comprising a first antigen-binding complex capable of specifically binding the first antigen, the method comprising detecting the presence of a photocleavable label in the sample, wherein the photocleavable label is conjugated to the first antigen-binding complex through a functional linker, wherein the first antigen-binding complex is non-covalently bound to the first antigen forming an antigen-bound antigen-binding complex of formula (I):

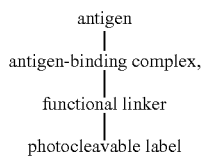

wherein the presence of the photocleavable label is indicative of the presence of the first antigen.

In some embodiments, the methods further comprise photocleaving the photocleavable label. Photocleaving may comprise exposing the sample to ultraviolet light.

In some embodiments, the photocleavable label comprises a reporter moiety covalently conjugated to a photocleavable moiety. The photocleavable moiety may be a 2-nitrobenzyl group, a benzoin group, a coumarinyl group, or a p-hydroxyphenacyl group. In various embodiments, the photocleavable moiety is a 2-nitrobenzyl group. In certain embodiments, the 2-nitrobenzyl group comprises a substitution on the α-carbon and/or on the benzene ring.

In some embodiments, the functional linker is a single-stranded oligonucleotide, an at least partially double-stranded oligonucleotide, a peptide, or an alkanediyl$_{(C \leq 16)}$. In certain embodiments, the at least partially double-stranded oligonucleotide is a hairpin oligonucleotide. In certain embodiments, the at least partially double-stranded oligonucleotide is a fully double-stranded oligonucleotide.

In some embodiment, the first antigen-binding complex is defined by formula (II):

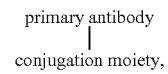

wherein the first antigen-binding complex comprises a primary antibody bound to a conjugation moiety, wherein the antigen-bound antigen-binding complex is further defined by formula (III):

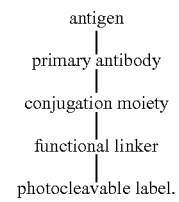

In some embodiments, the primary antibody is modified by at least one reducing agent, such as, for example, TCEP or 2-MEA. In some embodiments, the conjugation moiety is a heterobifunctional linker, such as, for example, Sulfo-SMCC or SM(PEG)n. In some embodiments, the conjugation moiety is covalently attached to the primary antibody. In some embodiments, the conjugation moiety is covalently attached to the functional linker. In some embodiments, the functional linker is a partially double-stranded oligonucleotide with a C6 amino modification on the 5' end and a photocleavable label on the 3' end.

In some embodiments, the first antigen-binding complex is defined by the formula (IV):

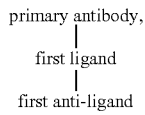

wherein the first antigen-binding complex comprises a primary antibody covalently conjugated to a first ligand, wherein the first ligand is non-covalently bound to a first anti-ligand, wherein the antigen-bound antigen-binding complex is further defined by formula (V):

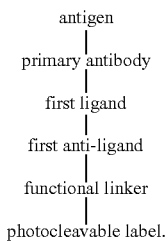

In some embodiments, the methods further comprise sequentially contacting the sample with the primary antibody and the first anti-ligand. In other embodiments, the methods further comprise simultaneously contacting the sample with the primary antibody and the first anti-ligand. The first ligand may be biotin, avidin or streptavidin, or a first single-stranded oligonucleotide. The first anti-ligand may be avidin or streptavidin, biotin, or a second single-stranded oligonucleotide at least partially complementary to the first single-stranded oligonucleotide.

In some embodiments, the photocleavable label is covalently bound to the first anti-ligand through a functional linker. In some embodiments, two occurrences of the same photocleavable label are covalently bound to the first anti-ligand through a functional linker. In other embodiments, two different photocleavable labels are covalently bound to the first anti-ligand through a functional linker. The functional linker may be a single-stranded oligonucleotide, an at least partially double-stranded oligonucleotide (such as, but not limited to, a hairpin oligonucleotide), a peptide, or an alkanediyl$_{(C \leq 16)}$. In certain embodiments, the at least partially double-stranded oligonucleotide is a fully double-stranded oligonucleotide.

In some embodiments, the first antigen-binding complex is defined by formula (VI):

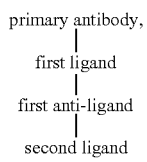

wherein the first antigen-binding complex comprises a primary antibody covalently bound to a first ligand, wherein the first ligand is non-covalently bound to a first anti-ligand, wherein the second ligand is non-covalently bound to the first anti-ligand, wherein the antigen-bound antigen-binding complex is further defined by formula (VII):

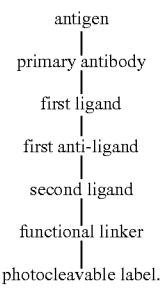

In some embodiments, the methods further comprise sequentially contacting the sample with the primary antibody, the first anti-ligand, and/or the second ligand. In other embodiments, the methods further comprise simultaneously contacting the sample with the primary antibody, the first anti-ligand, and/or the second ligand. The first ligand may be biotin, avidin, or an anti-avidin antibody. The first anti-ligand may be avidin or streptavidin or biotin. The second ligand may be biotin, avidin, or an anti-avidin antibody. In some aspects, the first anti-ligand comprises a single-stranded oligonucleotide and the second ligand comprises a second single-stranded oligonucleotide at least partially complementary to the first single-stranded oligonucleotide.

In some embodiments, the photocleavable label is covalently bound to the second ligand through a functional linker. In some embodiments, two occurrences of the same photocleavable label are covalently bound to the second ligand through a functional linker. In other embodiments, two different photocleavable labels are covalently bound to the second ligand through a functional linker. The functional linker may be a single-stranded oligonucleotide, an at least partially double-stranded oligonucleotide (such as, but not limited to, a hairpin oligonucleotide), a peptide, or an alkanediyl$_{(C \leq 16)}$. In certain embodiments, the at least partially double-stranded oligonucleotide is a fully double-stranded oligonucleotide.

In some embodiments, the first antigen-binding complex is defined by formula (VIII):

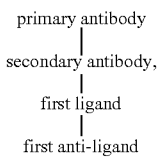

wherein the first antigen-binding complex comprises a primary antibody bound by a secondary antibody, wherein the secondary antibody is covalently bound to a first ligand, wherein the first ligand is non-covalently bound to a first anti-ligand, wherein the antigen-bound antigen-binding complex is further defined by formula (IX):

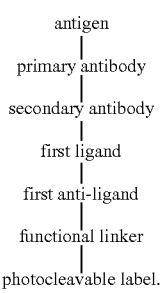

In some embodiments, the methods further comprise sequentially contacting the sample with the primary antibody, the secondary antibody, and/or the first anti-ligand. In other embodiments, the methods further comprise simultaneously contacting the sample with the primary antibody, the secondary antibody, and/or the first anti-ligand. The first ligand may be biotin, avidin or streptavidin, or a first single-stranded oligonucleotide. The first anti-ligand may be avidin, streptavidin, biotin, anti-avidin, or a second single-stranded oligonucleotide at least partially complementary to the first single-stranded oligonucleotide.

In some embodiments, the photocleavable label is covalently bound to the first anti-ligand through a functional linker. In some embodiments, two occurrences of the same photocleavable label are covalently bound to the first anti-ligand through a functional linker. In other embodiments, two different photocleavable labels are covalently bound to the first anti-ligand through a functional linker. The functional linker may be a single-stranded oligonucleotide, an at least partially double-stranded oligonucleotide (such as, but not limited to, a hairpin oligonucleotide), a peptide, or an alkanediyl$_{(C \leq 16)}$. In certain embodiments, the at least partially double-stranded oligonucleotide is a fully double-stranded oligonucleotide.

In some embodiments, the first antigen-binding complex is defined by formula (X):

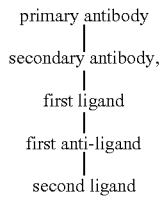

wherein the first antigen-binding complex comprises a primary antibody bound by a secondary antibody, wherein the secondary antibody is covalently bound to a first ligand, wherein the first ligand is non-covalently bound to a first anti-ligand, wherein the second ligand is non-covalently bound to the first anti-ligand, wherein the antigen-bound antigen-binding complex is further defined by formula (XI):

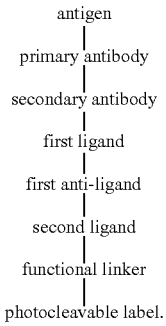

In some embodiments, the methods further comprise sequentially contacting the sample with the primary antibody, the secondary antibody, the first anti-ligand, and/or the second ligand. In other embodiments, the methods further comprise simultaneously contacting the sample with the primary antibody, the secondary antibody, the first anti-ligand, and/or the second ligand. The first ligand may be biotin or avidin or streptavidin. The first anti-ligand may be avidin or streptavidin or biotin. The second ligand may be biotin or avidin or streptavidin. In some aspects, the first anti-ligand comprises a single-stranded oligonucleotide and the second ligand comprises a second single-stranded oligonucleotide at least partially complementary to the first single-stranded oligonucleotide.

In some embodiments, the photocleavable label is covalently bound to the second ligand through a functional linker. In some embodiments, two occurrences of the same photocleavable label are covalently bound to the second ligand through a functional linker. In other embodiments, two different photocleavable labels are covalently bound to the second ligand through a functional linker. The functional linker may be a single-stranded oligonucleotide, an at least partially double-stranded oligonucleotide (such as, but not limited to, a hairpin oligonucleotide), a peptide, or an alkanediyl$_{(C \leq 16)}$. In certain embodiments, the at least partially double-stranded oligonucleotide is a fully double-stranded oligonucleotide.

In some embodiments, the first antigen-binding complex is defined by formula (XII):

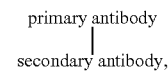

wherein the first antigen-binding complex comprises a primary antibody bound by a secondary antibody, wherein the secondary antibody is covalently bound to the photocleavable label through a functional linker, wherein the antigen-bound antigen-binding complex is further defined by formula (XIII):

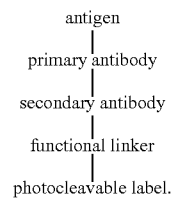

In some embodiments, the methods further comprise sequentially contacting the sample with the primary antibody and the secondary antibody. In other embodiments, the methods further comprise simultaneously contacting the sample with the primary antibody and the secondary antibody.

In some embodiments, the photocleavable label is covalently bound to the secondary antibody through a functional linker. In some embodiments, two occurrences of the same photocleavable label are covalently bound to the secondary antibody through a functional linker. In other embodiments, two different photocleavable labels are covalently bound to the secondary antibody through a functional linker. The functional linker may be a single-stranded oligonucleotide, an at least partially double-stranded oligonucleotide (such as, but not limited to, a hairpin oligonucleotide), a peptide, or an alkanediyl$_{(C \leq 16)}$. In certain embodiments, the at least partially double-stranded oligonucleotide is a fully double-stranded oligonucleotide.

In some embodiments, the first antigen-binding complex comprises an aptamer, wherein the aptamer is covalently bound to the photocleavable label through a functional linker, wherein the antigen-bound antigen-binding complex is further defined by formula (XIV):

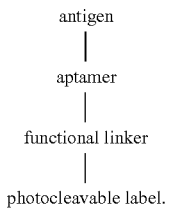

antigen
|
aptamer
|
functional linker
|
photocleavable label.

In some embodiments, the methods further comprise contacting the sample with the aptamer.

In some embodiments, the methods are defined as methods of detecting the presence of at least two antigens in the sample, the methods further comprising detecting the presence of at least a second photocleavable label in the sample, wherein the second photocleavable label is conjugated to a second antigen-binding complex through a functional linker, wherein the second antigen-binding complex is bound to the second antigen, wherein the presence of the second photocleavable label is indicative of the presence of the second antigen. Likewise, the methods may be defined as methods of detecting the presence of at least three antigens in the sample, the methods further comprising detecting the presence of at least a third photocleavable label in the sample, wherein the third photocleavable label is conjugated to a third antigen-binding complex through a functional linker, wherein the third antigen-binding complex is bound to the third antigen, wherein the presence of the third photocleavable label is indicative of the presence of the third antigen.

In some embodiments, detecting the first photocleavable label and detecting the second, and optionally the third, photocleavable label are performed simultaneously. In some embodiments, the first antigen-binding complex and the second antigen-binding complex each comprise a unique photocleavable label. In other embodiments, the first antigen-binding complex and the second antigen-binding complex each comprise the same photocleavable label. In some embodiments, detecting the first photocleavable label and detecting the second photocleavable label are performed sequentially.

In some embodiments, the methods further comprise photocleaving the first photocleavable label prior to detecting the second photocleavable label. In some embodiments, the methods further comprise photocleaving the second photocleavable label following detection of the second photocleavable label. In some embodiments, the methods further comprise photocleaving the first and second photocleavable labels simultaneously. Photocleaving may comprise exposing the sample to ultraviolet light.

In some embodiments, the methods further comprise detecting at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in the sample. Some antigens may be detected simultaneously while other antigens are detected sequentially within the same sample. For simultaneous detection, each antigen-binding complex comprises a unique photocleavable label. At least 2, 3, 4, 5, 6, 7, 8, 9, 10, 11, 12, 13, 14, 15, 16, 17, 18, 19, or 20 different antigens may be detected simultaneously. In methods of simultaneous antigen detection, each antigen-binding complex may be added to the sample sequentially followed by a single detection step. Alternatively, some of the antigen-binding complexes may be added simultaneously. In various embodiments, at least a portion of the steps of the method may be automated. In some embodiments, all of the steps of the method may be automated.

In some embodiments, the photocleavable label is a colorimetric dye, a fluorescent dye, a radioactive label, a chemiluminescent group, or a bioluminescent group. In some embodiments, the sample is a tissue section, biopsy sample, cell culture sample, cell smear, or protein lysate.

Certain embodiments include an apparatus configured to perform any of the methods disclosed herein. Particular embodiments include: an imaging system configured to image a sample; a sample chamber comprising a fluid inlet and a fluid outlet; and a fluid control system comprising a plurality of reservoirs, where the fluid control system is in fluid communication with the fluid inlet and the fluid outlet of the sample chamber.

In some embodiments, the fluid control system is configured to provide automated serial staining of the sample. In specific embodiments, the fluid control system further comprises a valve in fluid communication with the sample chamber and with the plurality of reservoirs. In certain embodiments, the valve is a rotary valve. Particular embodiments further comprise a light source configured to photocleave the first antigen-binding complex from the first antigen. In some embodiments, the plurality of reservoirs comprises a first reservoir containing an imaging solution, a second reservoir containing a wash solution, a third reservoir containing a cleavage solution, a fourth reservoir containing a buffer solution, a fifth reservoir containing a hybridization wash solution, and/or a sixth reservoir containing a hybridization solution.

In specific embodiments, the fluid control system further comprises a valve in fluid communication with the sample chamber and with the first, second, third, fourth, fifth, and sixth reservoirs. In certain embodiments, the sample chamber comprises a microscope slide, a coverslip, and a gasket disposed between the microscope slide and coverslip.

In particular embodiments, the fluid inlet and the fluid outlet of the sample chamber are coupled to the coverslip. In some embodiments, the sample chamber is coupled to a platform configured to move in an X-Y plane. In specific embodiments, the fluid outlet of the sample chamber is coupled to a fluid transport device. In certain embodiments, the fluid transport device is a syringe pump. In particular embodiments, the imaging system comprises: a microscope; a light source; a light guide adapter; and a camera.

Particular embodiments include an apparatus for detecting the presence of at least a first antigen on or in a sample, the apparatus comprising: a sample chamber comprising a fluid inlet and a fluid outlet; an imaging system configured to image a sample in the sample chamber; a light source configured to photocleave a first antigen-binding complex from a first antigen on or in the sample; and a fluid control system in fluid communication with the fluid inlet and the fluid outlet of the sample chamber, where the fluid control system comprises a plurality of reservoirs in fluid communication with the sample chamber.

In specific embodiments, the fluid control system is configured to provide automated serial staining of the sample. In particular embodiments, the imaging system is configured to provide automated imaging of the sample. In some embodiments, the plurality of reservoirs comprises a first reservoir containing an imaging solution, a second reservoir containing a wash solution, a third reservoir containing a cleavage solution, a fourth reservoir containing a buffer solution, a fifth reservoir containing a hybridization wash solution, and a sixth reservoir containing a hybridization solution. In certain embodiments, the fluid control system further comprises a valve in fluid communication with the sample chamber and with the first, second, third, fourth, fifth, and sixth reservoirs. In particular embodiments, the valve is a rotary valve. In some embodiments, the sample chamber comprises a microscope slide, a coverslip, and a gasket disposed between the microscope slide and coverslip.

In specific embodiments, the sample chamber is coupled to a platform configured to move in an X-Y plane. In certain embodiments, the fluid inlet and the fluid outlet of the sample chamber are coupled to the coverslip. In particular embodiments, the fluid outlet of the sample chamber is coupled to a fluid transport device. In some embodiments, the fluid transport device is a syringe pump. In specific embodiments, imaging system comprises a microscope, a light source, a light guide adapter, and a camera. In certain embodiments, the apparatus is configured to stain and image a plurality of sample chambers simultaneously or via random access.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Exemplary partially double-stranded biotin-oligonucleotide-photocleavable fluorescent dye. The sequence of the top strand is provided as SEQ ID NO: 1; the sequence of the bottom strand is provided as SEQ ID NO: 2.

FIG. 4. Exemplary single-stranded biotin-oligonucleotide-photocleavable label complexed with a single photocleavable fluorescent dye. The sequence of each example is provided as SEQ ID NO: 3.

FIG. 5. Exemplary double-stranded biotin-oligonucleotide-photocleavable label complexed with two photocleavable fluorescent dyes of the same color. The sequence of the top strand of the first (Cy5) example is provided as SEQ ID NO: 3; the sequence of the bottom strand of the first (Cy5) example is provided as SEQ ID NO: 4. The sequence of the top strand of the second (AF594) example is provided as SEQ ID NO: 5; the sequence of the bottom strand of the second (AF594) example is provided as SEQ ID NO: 6. The sequence of the top strand of the third (AF532) example is provided as SEQ ID NO: 7; the sequence of the bottom strand of the third (AF532) example is provided as SEQ ID NO: 8. The sequence of the top strand of the fourth (AF488) example is provided as SEQ ID NO: 9; the sequence of the bottom strand of the fourth example (AF488) is provided as SEQ ID NO: 10.

FIG. 6. Exemplary hairpin biotin-oligonucleotide-photocleavable label with a single photocleavable fluorescent dye. The sequence of the first (Cy5) example is provided as SEQ ID NO: 11; the sequence of the second (AF594) example is provided as SEQ ID NO: 12; the sequence of the third (AF532) example is provided as SEQ ID NO: 13; the sequence of the fourth (AF488) example is provided as SEQ ID NO: 14.

FIG. 7. Exemplary photocleavable label covalently attached to a biotin molecule through a functional linker. The functional linker can be a nucleic acid, peptide, or fatty acid chain.

FIGS. 9A-E. Efficiency of photocleavage. FIG. 9A shows an image of the stained tissue section before cleavage. FIG. 9B shows an image of the stained section following 2 min of cleavage by UV 365 nm exposure. FIG. 9C shows an image of the stained section following a buffer refresh. FIG. 9D is an image of a different FOV showing the cleavage boundary (the upper left corner was cleaved). FIG. 9E is an image pixel intensity profile along the line across FIGS. 9A-C showing the image brightness change after cleavage and after wash.

FIGS. 10A-H. Time course of photocleavage using various PCLs. FIG. 10A shows the trace of maximum signal intensity. FIG. 10B shows the trace of absolute difference in signal (signal to background). FIG. 10C shows that trace of relative difference in signal (signal to background) as a percentage of the maximal signal. FIG. 10D shows the images of the Standard Duplex PCL before and after photocleavage in the center of the field. FIG. 10E shows the images of the Long Duplex PCL before and after photocleavage. FIG. 10F shows the images of the Short PCL before and after photocleavage. FIG. 10G shows the images of the Single Biotin Duplex PCL before and after photocleavage. FIG. 10H shows the images of the oligonucleotide having a photocleavable biotin (IDT Duplex PCL) both before and after cleavage.

FIG. 19A. Schematic of three consecutive staining and imaging cycles. FIG. 19B. A stitched image of 25 pictures taken with a 20× objective (5×5) showing Collagen, ALCAM and Hoechst. The dotted square outlines an area magnified and split into channels in FIGS. 19C-E. FIG. 19C. ALCAM, CD44, Hoechst. FIG. 19D. SMA, cytokeratin, Hoechst. FIG. 19E. Fibronectin, Histone H3, Hoechst.

FIGS. 21A-C. FIG. 21A. Post-cleavage image of multiplex stained tissue in FIG. 20. All signal was released after one photocleaving event. FIG. 21B. shows trace of relative percent of total signal over total cleavage time. FIG. 21C. shows the trace of maximum signal intensity.

DESCRIPTION OF ILLUSTRATIVE EMBODIMENTS

Figure 1:
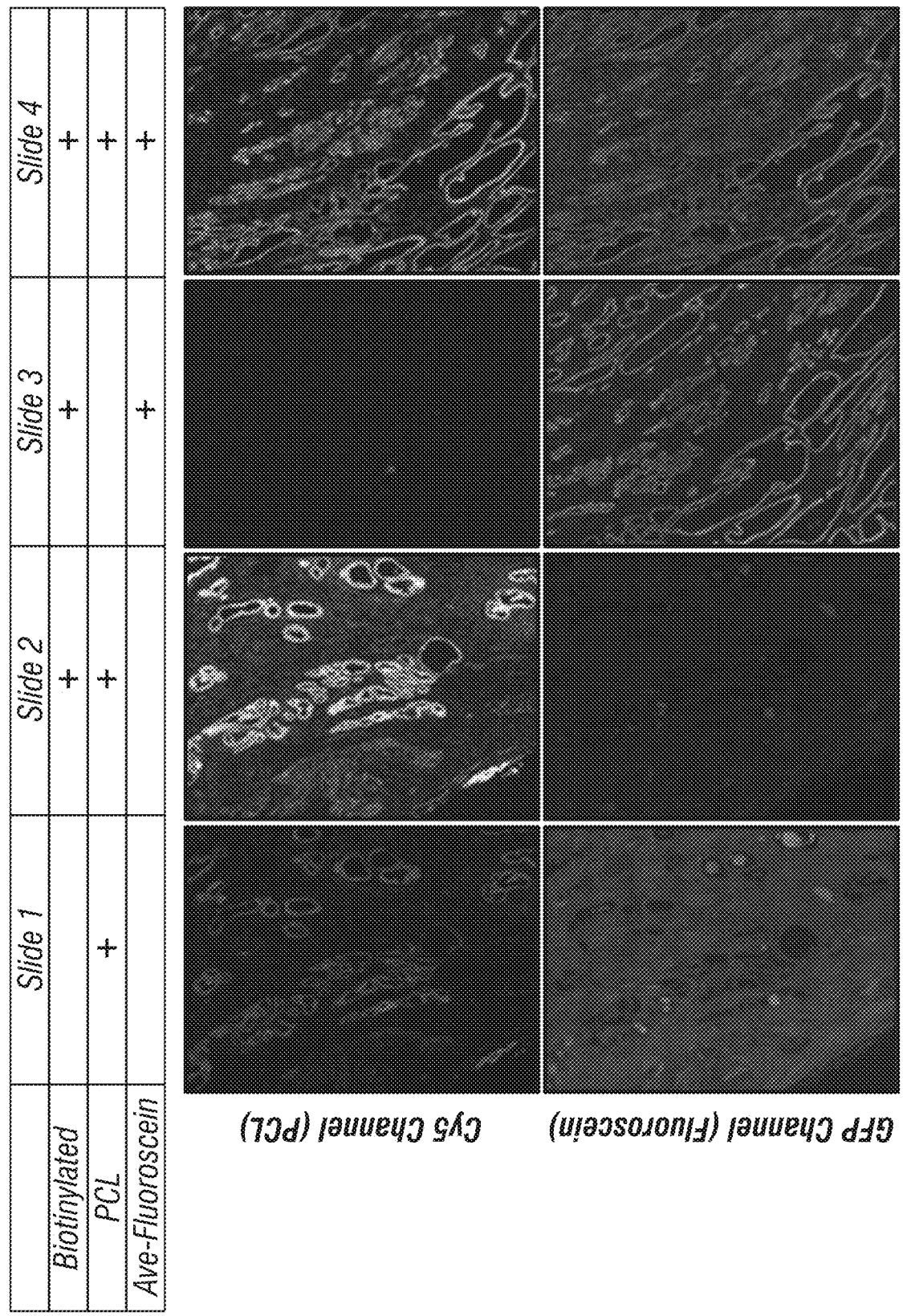
FIG. 1. Detection of an antigen in a tissue section using a single-stranded biotin-oligonucleotide-photocleavable Cy5 fluorescent dye. Included as controls are biotinylated and fluorescein-labeled probes.
Figure 3:
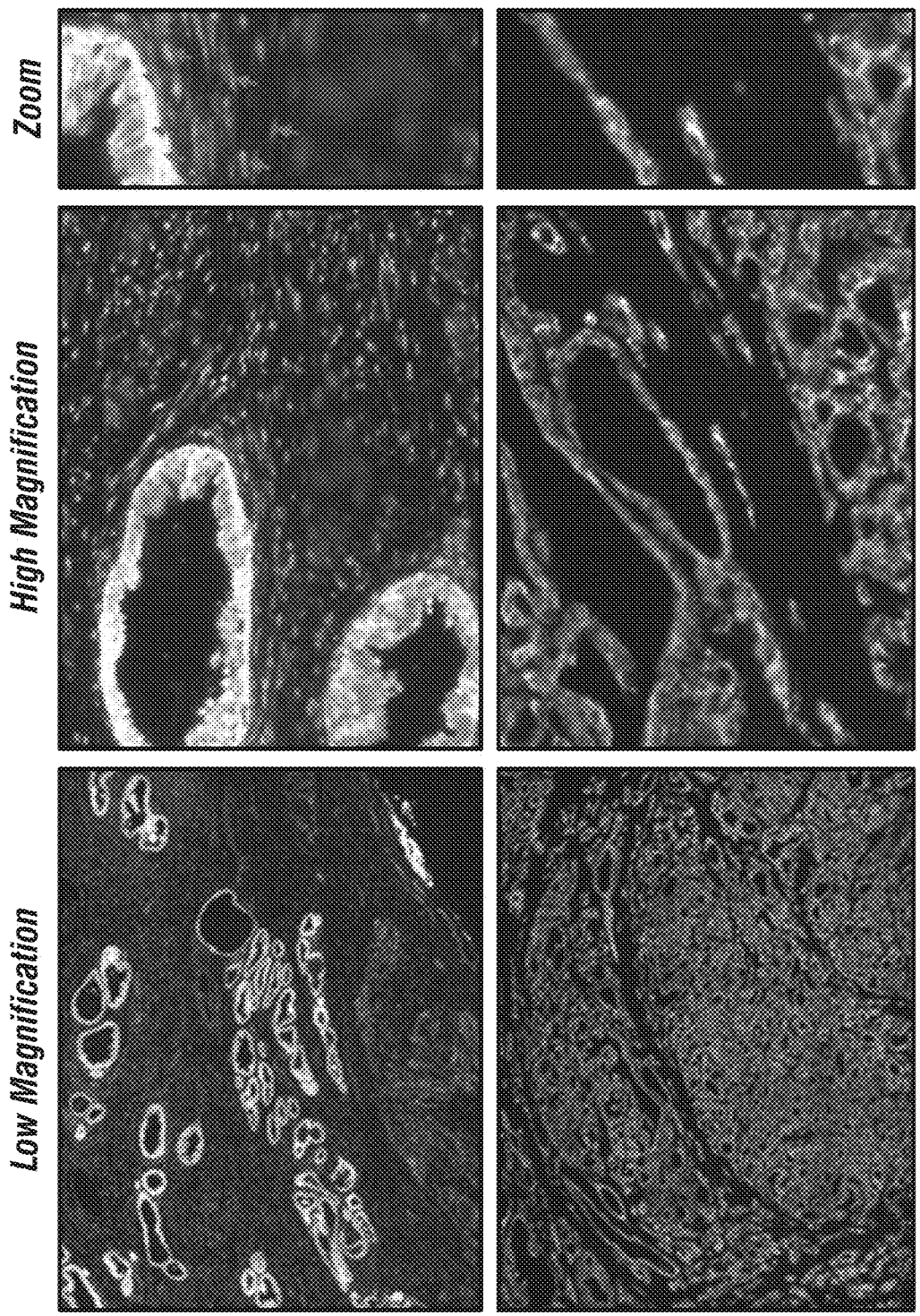
FIG. 3. Detection of an antigen in a tissue section using a single-stranded and a partially double-stranded biotin-oligonucleotide-photocleavable Cy5 fluorescent dye.

Immunofluorescent detection of antigens in fixed tissue specimens is used routinely in clinical practice and research laboratories. Current methods are limited to the detection of one to four antigens per tissue section. Consequently, the detection of additional antigens requires multiple independent stains on separate sections and limits the co-localization of antigens on a single section. Additionally, current methods are exceedingly time-consuming because staining and imaging are disconnected processes.

An automated Next Generation Histology (NGH) platform for formalin-fixed paraffin embedded (FFPE) tissue sections was developed to overcome these limitations. The platform was designed to use a probe in which the traditional fluorescent tag is replaced with a novel photocleavable fluorophore that is released by UV irradiation. The photocleavable label enables rapid cycles of repeated staining in the same tissue section without the need to remove the antigen-detecting antibody. The NGH platform also includes automated fluidics for reduced hands-on time and a four-color epi-fluorescence microscopy imaging system for multiplex PCL detection on a single platform.

I. METHODS OF ANTIGEN DETECTION

In various embodiments, the invention provides methods of detecting the presence of at least a first antigen on, or in, a sample comprising various incubating steps required to build an "antigen-binding complex" to which a photocleavable label is conjugated via a functional linker.

In some embodiments, the invention provides methods of detecting the presence of at least a first antigen on or in a sample comprising the following steps:
1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Perform first ligand/first anti-ligand block (e.g., avidin or streptavidin/biotin block)
5. Incubate with primary antibody
6. Wash
7. Incubate with first ligand-conjugated (e.g., biotinylated) secondary antibody
8. Wash
9. Incubate with first anti-ligand (e.g., avidin or streptavidin)
10. Wash
11. Incubate with second ligand (e.g., biotin)-bound photocleavable label
12. Wash
13. Detect signal from photocleavable label
14. Photocleave
15. Optionally, confirm successful photocleavage by detecting an absence of signal from the photocleavable label In some variations, steps 7 and 9 may be performed simultaneously; in these variations, the first ligand-conjugated (e.g., biotinylated) secondary antibody and the first anti-ligand (e.g., avidin or streptavidin) are added at the same time and step 8 is not performed. In some embodiments, they are in the same solution. In some variations, steps 5 through 15 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some embodiments, the invention provides methods of detecting the presence of at least a first antigen on or in a sample comprising the following steps:
1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Perform first ligand/first anti-ligand block (e.g., avidin or streptavidin/biotin block)
5. Incubate with primary antibody
6. Wash 7. Incubate with first ligand-conjugated (e.g., biotinylated) secondary antibody
8. Wash
9. Incubate with first anti-ligand (e.g., avidin or streptavidin)-bound photocleavable label
10. Wash
11. Detect signal from photocleavable label
12. Photocleave
13. Optionally, confirm successful photocleavage by detecting an absence of signal from the photocleavable label In some variations, steps 7 and 9 may be performed simultaneously; in these variations, the first ligand-conjugated (e.g., biotinylated) secondary antibody and the first anti-ligand (e.g., avidin or streptavidin) are added at the same time and step 8 is not performed. In some embodiments, they are in the same solution. In some variations, steps 5 through 13 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In another aspect, the invention provides a method of detecting the presence of at least a first antigen on or in a sample comprising the following steps:
1. Prepare the sample for antigen detection as needed (e.g., deparafinization, rehydration), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Incubate with primary antibody
5. Wash
6. Incubate with a secondary antibody conjugated to a photocleavable label
7. Wash
8. Detect signal from photocleavable label
9. Photocleave
10. Optionally, confirm successful photocleavage by detecting an absence of signal from the photocleavable label In some variations, steps 4 through 10 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some embodiments, the invention provides methods of detecting the presence of at least a first antigen on or in a sample comprising the following steps:
1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Perform first ligand/first anti-ligand block (e.g., avidin or streptavidin/biotin block)
5. Incubate with first ligand-conjugated (e.g., biotinylated) primary antibody
6. Wash
7. Incubate with first anti-ligand (e.g., avidin or streptavidin)-bound photocleavable label
8. Wash
9. Detect signal from photocleavable label
10. Photocleave
11. Optionally, confirm successful photocleavage by detecting an absence of signal from the photocleavable label In some variations, steps 5 and 7 may be performed simultaneously; in these variations, the first ligand-conjugated (e.g., biotinylated) primary antibody and the first anti-ligand (e.g., avidin or streptavidin) are added at the same time and step 6 is not performed. In some embodiments, they are in the same solution. In some variations, steps 5 through 11 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some embodiments, the invention provides methods of detecting the presence of at least a first antigen on or in a sample comprising the following steps:
1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Perform first ligand/first anti-ligand block (e.g., avidin or streptavidin/biotin block)
5. Incubate with first ligand-conjugated (e.g., biotinylated) primary antibody
6. Wash
7. Incubate with first anti-ligand (e.g., avidin or streptavidin)
8. Wash
9. Incubate with second ligand (e.g., biotin)-bound photocleavable label
10. Wash
11. Detect signal from photocleavable label
12. Photocleave
13. Optionally, confirm successful photocleavage by detecting an absence of signal from the photocleavable label In some variations, steps 5 and 7 may be performed simultaneously; in these variations, the first ligand-conjugated (e.g., biotinylated) primary antibody and the first anti-ligand (e.g., avidin or streptavidin) are added at the same time and step 6 is not performed. In some embodiments, they are in the same solution. In some variations, steps 5 through 13 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some embodiments, the invention provides methods of detecting the presence of at least a first antigen on or in a sample comprising the following steps:

1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Incubate with a non-protein first ligand-bound photocleavable label
5. Wash
6. Detect signal from photocleavable label
7. Photocleave
8. Optionally, confirm successful photocleavage by detecting an absence of signal from the photocleavable label In some variations, steps 4 through 8 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some variations, the non-protein first ligand can be an aptamer, a carbohydrate, a nucleic acid (e.g., DNA), a hormone, or a small molecule.

In some embodiments, the invention provides methods of detecting the presence of at least a first antigen on or in a sample comprising the following steps:
1. Prepare the sample for antigen detection as needed (e.g., deparafinization, rehydration, etc.), methods for which are well known to one of skill in the art
2. Perform antigen retrieval (e.g., heat+salt+pH)
3. Perform non-specific antigen blocking (e.g., BSA, serum or a non-protein based blocking agent such as Tween®-20)
4. Perform first ligand/first anti-ligand block (e.g., avidin or streptavidin/biotin block)
5. Incubate with first ligand-conjugated (e.g., biotinylated) aptamer
6. Wash
7. Incubate with first anti-ligand (e.g., avidin or streptavidin)
8. Wash
9. Incubate with second ligand (e.g., biotin)-bound photocleavable label
10. Wash
11. Detect signal from photocleavable label
12. Photocleave
13. Optionally, confirm successful photocleavage by detecting an absence of signal from the photocleavable label In some variations, steps 5 and 7 may be performed simultaneously; in these variations, the first ligand-conjugated (e.g., biotinylated) aptamer and the first anti-ligand (e.g., avidin or streptavidin) are added at the same time and step 6 is not performed. In some embodiments, they are in the same solution. In some variations, steps 5 through 13 may be repeated for a second (or more) antigen. In some embodiments, steps of the method may be repeated at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 times to detect a plurality of antigens in the sample. For example, the method may be used to detect the presence of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 antigens in a single sample.

In some embodiments, the methods provided herein may be used in conjunction and/or combination with known techniques for antigen detection, including, but not limited to, Western blotting, microarray, enzyme-linked immunosorbent assay (ELISA), reverse phase protein array (RPPA), and immunohistochemistry (based on colorimetric or fluorescent read-outs).

In some embodiments, a sample will need to be prepared for antigen detection prior to being incubated with the various components of an antigen-binding complex. In some variations, a target cell will need to be fixed, e.g., by adding chemical fixatives, such as aldehydes or paraformaldehyde, to crosslink, alcohols to precipitate, oxidizing agents, mercurials, and picrates. In some variations, cell permeability will need to be increased by, e.g., adding organic solvents, such as methanol and acetone, or detergents, such as Triton™-X 100, saponin, and Tween®-20. In some variations, blocking steps will need to be performed to reduce non-specific reactions by, e.g., adding bovine serum albumin, goat serum, fish skin gelatin, horse serum, swine serum, donkey serum, or rabbit serum.

In some embodiments, various incubating steps are performed to build the antigen-bound antigen-binding complex in the sample. In some cases, more than one component of an antigen-binding complex may be added to the sample simultaneously while others are added sequentially. In some cases, each component of an antigen-binding complex is added to the sample sequentially. In some cases, every component of an antigen-binding complex may be added to the sample simultaneously. The various incubating steps may be performed under conditions that favor an interaction between the primary antibody, aptamer, etc. and the target antigen that may be present in the sample, or alternatively/additionally, between a primary antibody and a secondary antibody, between a first ligand and a first anti-ligand, or between a first anti-ligand and a second ligand. Exemplary conditions that may be modulated to affect a desired interaction include temperature and pH. Exemplary temperatures for incubation steps include any temperature between 15° C. and 30° C., 18° C. and 27° C., or 20° C. and 25° C., or any range derivable therein. Exemplary temperature for incubation steps include, for example, 15° C., 16° C., 17° C., 18° C., 19° C., 20° C., 21° C., 22° C., 23° C., 24° C., 25° C., 26° C., 27° C., 28° C., 29° C., and 30° C. Exemplary pH values for incubation steps include any pH between 6 and 8, 6.2 and 7.8, or 6.5 and 7.5, or any range derivable therein. Exemplary pH values for incubation steps include 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

In some embodiments, washing steps are performed following various incubating steps to remove any components that are not specifically bound to the antigen-bound antigen-binding complex in the sample. Washing may be performed using a washing solution comprising, for example, water, a buffer solution (e.g., PBS), physiological saline, or a combination thereof.

In some embodiments, various components of an antigen-binding complex may be biotinylated. In biochemistry, biotinylation is the process of covalently attaching biotin to a protein, nucleic acid, or other molecule. Biotinylation is rapid, specific and is unlikely to perturb the natural function of the molecule due to the small size of biotin (MW=244.31 g/mol). Various methods are known in the art for biotinylating biological macromolecules, such as, for example, proteins and nucleic acids. See, e.g., Moritz and Wahle (2014); Hermanson (2013). Also, multiple biotin molecules can be conjugated to a molecule of interest. Proteins can be biotinylated chemically or enzymatically. Chemical biotinylation utilizes various conjugation chemistries to yield nonspecific biotinylation of amines, carboxylates, sulfhydryls and carbohydrates (e.g., NHS-coupling gives biotinylation of any primary amines in the protein). Enzymatic biotinylation results in biotinylation of a specific lysine within a certain sequence by a bacterial biotin ligase. Most chemical biotinylation reagents consist of a reactive group attached via a linker to the valeric acid side chain of biotin. As the biotin binding pocket in avidin/streptavidin is buried beneath the protein surface, biotinylation reagents possessing a longer linker are desirable, as they enable the biotin molecule to be more accessible to binding avidin/streptavidin/Neutravidin protein. This linker can also mediate the solubility of biotinylation reagents; linkers that incorporate poly(ethylene) glycol (PEG) can make water-insoluble reagents soluble or increase the solubility of biotinylation reagents that are already soluble to some extent. Oligonucleotides are readily biotinylated in the course of oligonucleotide synthesis by the phosphoramidite method using commercial biotin phosphoramidite. Upon the standard deprotection, the conjugates obtained can be purified using reverse-phase or anion-exchange HPLC.

In some embodiments, detecting a signal from a photocleavable label comprises measuring the signal generated from the antigen-bound antigen-binding complex present in the sample. Detecting may, for example, comprise measuring a signal generated by a fluorescent dye of the antigen-bound antigen-binding complex using a fluorescence microscope. The presence of a signal generated by, e.g., a fluorescent dye may indicate that the antigen is present in the sample. Thus, detecting may comprise determining the presence of the antigen in the sample. In some variations, detecting a signal may be defined as measuring a signal from a photocleavable label, where said measuring provides either a relative quantitative, absolute quantitative, or qualitative measure of the amount of the antigen present in the same.

In some embodiments described herein, the photocleavable label comprises a 2-nitrobenzyl or substituted 2-nitrobenzyl group, which may be efficiently photochemically cleaved, for example, with 365 nm UV light. See U.S. Patent Appl. Publ. 2010/0041041, which is incorporated herein by reference. It is generally understood that wavelengths >300 nm are used to minimize damage to DNA and proteins (Corrie, 2005) with several specific exemplary wavelengths other than 365 nm being 340 nm and 355 nm (Seo, 2005). As such, the terms "photocleaving" or "photocleave," as used herein, are meant to refer generally to the act of exposing a sample to a wavelength of light >300 nm so as to effect the cleavage of the photocleavable bond.

In some embodiments, after the photocleaving step, the method may further comprise repeating the incubating steps to build an antigen-binding complex on or in a sample and detecting a signal from the photocleavable label conjugated to an antigen-bound antigen-binding complex to detect the presence of a second antigen in the sample. For any given method of building an antigen-binding complex, after photocleavage of the label from the previously built antigen-binding complex, the steps of incubation to build the new antigen-binding complex and detecting a signal from the photocleavable label may be sequentially repeated at least once. In some variations, the steps may be sequentially repeated at least twice, three times, four times, five times, 10 times, 20 times, 30 times, 40 times, 50 times, 60 times, 70 times, 80 times, 90 times, or 100 times. In some variations, the photocleavable label may be subjected to conditions to effect photocleavage between each repetition of the steps. In some variations, the steps may be repeated once, twice, three times, four times, five times, six times, seven times, eight times, nine times, or 10 times consecutively before a photocleavage step is performed. In some variations, the photocleavable label conjugated to an antigen-binding complex in any given repetition may be the same or different from the label used in any previous repetition.

In some variations, the incubating steps to build the antigen-binding complex may be repeated once, twice, three times, four times, five times, six times, seven times, eight times, nine times, or 10 times consecutively before a detecting step is performed. In these variations, the photocleavable labels conjugated to each antigen-binding complex are different so that they can be distinguished during one detecting step, i.e., the labels are selected so that the overlap of the emission spectra of the various labels is minimized.

In some variations, the components of an antigen-binding complex used in each repetition may be the same or different from the components used in an antigen-binding complex from a previous cycle. In some variations, only the component that binds directly to the antigen is different, while the other components are the same.

II. PHOTOCLEAVABLE LABELS

Some aspects of the present invention are directed towards providing photocleavable labels with improved UV-cleavage rates for use in detection of multiple proteins in a single sample sequentially and/or simultaneously. Cleavage of the 2-nitrobenzyl or substituted 2-nitrobenzyl group with, e.g., 365 nm UV light allows for the next cycle of antigen detection to be performed without interference from the label(s) used in the previous cycle(s). Without being bound by theory, at least two factors have been found to influence UV-cleavage rates of substituted 2-nitrobenzyl groups: a) stereo-chemistry of the α-carbon substitution of the 2-nitrobenzyl group, and b) substitution on the benzyl ring.

The photocleavable labels are optionally conjugated to ribonucleoside triphosphates (NTPs) and deoxyribonucleoside triphosphates (dNTP). For example, a nucleotide or nucleoside compound may include a chemically or enzymatically cleavable group labeled with a reporter group, such as a fluorescent dye. The nucleotide and nucleoside compounds may include chemically or enzymatically removable protecting groups that are designed to terminate DNA synthesis. The presence of such cleavable groups labeled with fluorescent dyes on the nucleotide and nucleoside compounds can enhance the speed and accuracy of indirect detection of multiple proteins in a single sample. Examples of such nucleotide and nucleoside compounds include those disclosed in PCT Publn. Nos. WO 2003/006625, WO 2005/084367, WO 2008/070749, WO 2009/152353, WO 2013/040257, which are each incorporated herein by reference in their entirety. In some cases, an oligonucleotide may be produced that comprises a photocleavable linker (Gene Link Cat. No. 26-6888) or photocleavable spacer (Gene Link Cat. No. 26-6889), such as are commercially available. In addition, photocleavable nucleotide-fluorophore conjugates are available from Ambergen Technology. Also, the amino modifier C6-dT (Integrated DNA Technologies) can be used to make oligonucleotides with photocleavable fluorescent groups attached to a nucleoside base.

As used herein, the term "reporter" or "label" refers to a chemical moiety that is able to produce a detectable signal directly or indirectly. Examples of reporters include fluorescent dye groups, colorimetric dye groups, radioactive labels, or groups affecting a signal through chemiluminescent or bioluminescent means. Examples of fluorescent dye groups include xanthene derivate dyes (e.g., fluorescein and its derivatives, fluorescein isothiocyanate [FITC], carboxyfluorescein succinimidyl ester [CFSE], carboxyfluorescein diacetate succinimidyl ester [CFDA-SE], eosin Y, eosin B, rhodamine B, rhodamine 6G, rhodamine 123, rhodamine red-X [RRX], carboxytetramethylrhodamine [TAMRA], tetramethylrhodamine [TMR], isothiocyanate-derivative of rhodamine [TRITC], sulforhodamine 101, sulfonyl chloride derivative of sulforhodamine 101 [Texas Red], Oregon Green), BODIPY derivative dyes (e.g., BODIPY FL, BODIPY R6G, BODIPY TMR, BODIPY 581/591, BODIPY TR, BODIPY 630/650, BODIPY 650/665), coumarin derivative dyes (e.g., aminomethylcoumarin [AMCA]), allophycocyanin [APC], pyrene derivative dyes (e.g., Cascade Blue), 4',6-diaminidino-2-phenylindole [DAPI], DyLight dyes (e.g., DyLight™ 350, DyLight™ 405, DyLight™ 488, DyLight™ 550, DyLight™ 594, DyLight™ 633, DyLight™ 650, DyLight™ 680, DyLight™ 755, DyLight™ 800), phycoerythrin [PE], PI, peridinin-chlorophyll-protein [PerCP], cyanine derivative dyes (e.g., Cy®5.5, indodicarbocyanine (Cy®5), cyanine (Cy®2), indocarbocyanine (Cy®3), Cy®3B, Cy®3.5, Cy®7, Cy®7Q, oxacarbocyanine, thiacarbocyanine, merocyanine, phthalocyanine), anthracene derivative dyes (e.g., Draq-5, Draq-7, CyTRAK Orange, IRIS 2, IRIS 3, IRIS 3.5, IRIS 5, IRIS 5.5, IRIS 7G), eFluor dyes (e.g., eFluor® 450, PE-eFluor® 615, eFluor® 660, eFluor® 710, PE-eFluor® 610, PerCP-eFluor® 710, APC-eFluor® 780), FluoProbes dyes (FluoProbes 390, FluoProbes 488, FluoProbes 532, FluoProbes 547H, FluoProbes 594, FluoProbes 647H, FluoProbes 682, FluoProbes 752, FluoProbes 782), GFP, IRDye 800, Pacific Blue, Pacific Green, Pacific Orange, pyrene, phycobiliprotein, Quasar® dyes (e.g., Quasar® 570, Quasar® 670, Quasar® 705), SNAFL, sulfocyanine derivative dyes (e.g., sulfo-Cy3, sulfo-Cy5, sulfo-Cy7), Tokyo Green, Alexa Fluor® dyes (e.g., ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 635, ALEXA FLUOR® 647, ALEXA FLUOR® 660, ALEXA FLUOR® 680, ALEXA FLUOR® 700, ALEXA FLUOR® 750, ALEXA FLUOR® 790), squaraine dyes (e.g., Seta™ dyes, SeTau dyes, Square dyes), or combinations thereof. Additional examples of fluorescent dye groups that may be used in some embodiments of the present invention are disclosed throughout this Specification and in Haugland, 2005 and U.S. Pat. Nos. 4,439,356 & 5,188,934, which are incorporated by reference herein. Fluorescent dyes can be attached to biological macromolecules (i.e., proteins, nucleic acids, and fatty acid chains) via specific functional groups, such as amino groups (e.g., via succinimide, isothiocyanate or hydrazine), carboxyl groups (e.g., via carbodiimide), thiol (e.g., via maleimide or acetyl bromide), azide (e.g., via click chemistry), or non-specifically (glutaraldehyde) or non-covalently (e.g., via hydrophobicity, etc.). See, e.g., Proudnikov and Mirzabekov, 1996; Riedel et al., 2012. Examples of radioactive labels that may be used as reporters in some embodiments of the present invention, which are well known in the art, include $^{35}S$, $^{3}H$, $^{32}P$, or $^{33}P$. Examples of reporters that function by chemiluminescent or bioluminescent means and that may be used as reporters in some embodiments of the present invention are described in Nieman, 1989; Givens & Schowen, 1989; Orosz et al., 1996; and Hastings, 1983, which are incorporated by reference herein.

The photocleavable label of an antigen-binding complex used in each sequential repetition of a method disclosed herein may be the same or different than any photocleavable label used in an antigen-binding complex for a previous repetition on the same sample. In some cases, a photocleavable label may be comprised of multiple reporters that in combination provide a unique signal different from the signals of any of the reporter used singularly.

The photocleavable labels of each of the antigen-binding complexes used simultaneously in a multiplex repetition of a method disclosed herein are preferably different to allow for each reporter to be distinguishable from the others. In other words, in the case of fluorescent reporters, each fluorescent reporter of a plurality of antigen-binding complexes may be selected in such a manner that an overlap among emission spectrum of each fluorescent reporter is minimized. In some cases, two different dyes may be used simultaneously but imaged independently to provide the location. The number of different photocleavable labels that may be used simultaneously in a multiplex repetition of a method disclosed herein is two, three, four, five, six, seven, eight, nine, 10, 11, 12, 13, 14, or 15.

III. APPARATUS

Figure 13:
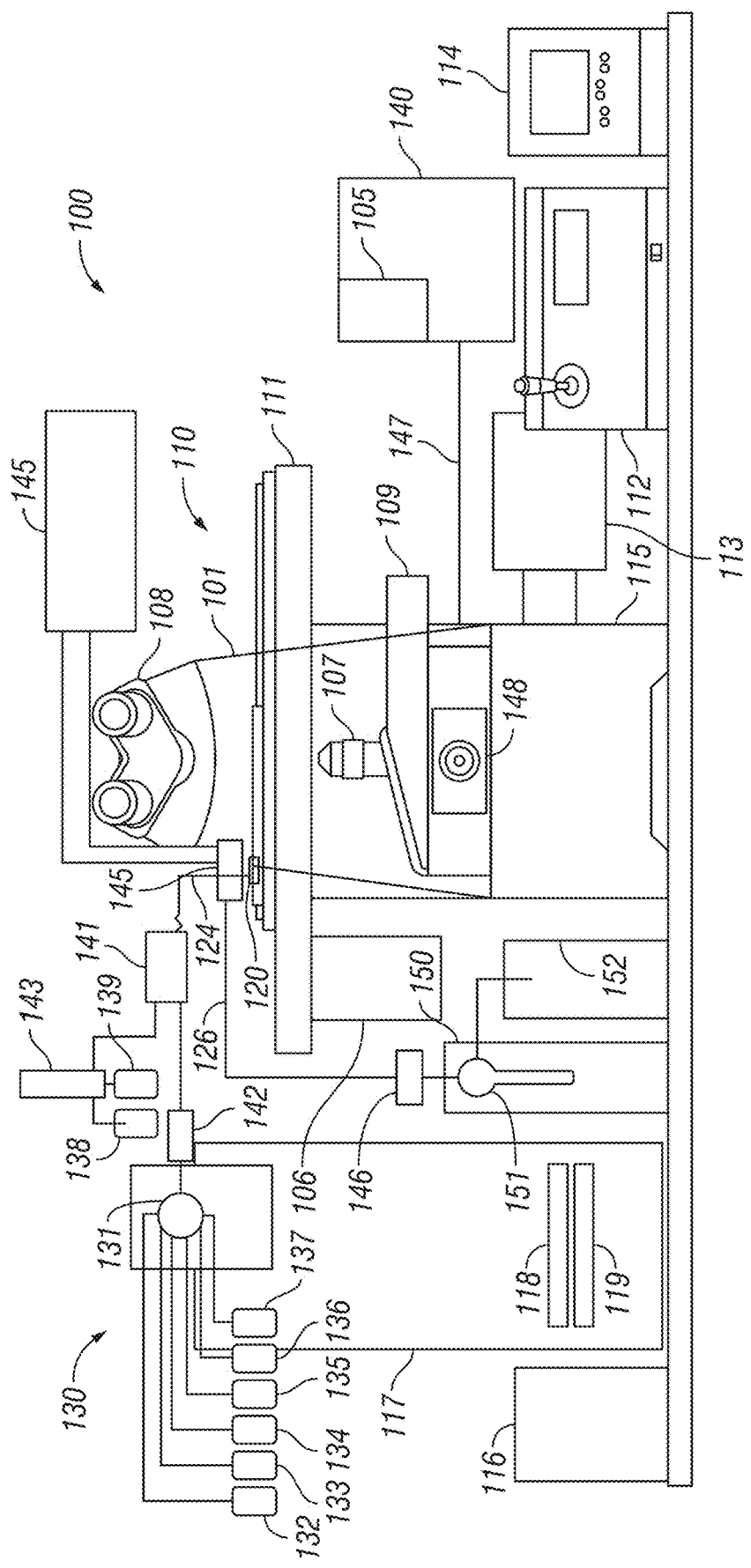
FIG. 13. Schematic of an apparatus according to exemplary embodiments disclosed herein.

As previously mentioned, exemplary methods disclosed herein may be performed via an automated Next Generation Histology (NGH) apparatus. Referring initially to FIG. 13, a schematic is provided of one exemplary embodiment of such an apparatus 100. Apparatus 100 can enable multiple, rapid cycles of staining in the same tissue section of a sample without the need to remove an antigen-detecting antibody. As discussed further below, apparatus 100 also includes automated fluidics for reduced hands-on time and a microscopy imaging system for multiplex PCL detection. In the embodiment shown, apparatus 100 comprises an imaging system 110, a sample chamber 120, and a fluid control system 130.

In the embodiment shown, fluid control system 130 comprises a valve 131 in fluid communication with sample chamber 120 and with a plurality of reservoirs 132-137. Reservoirs 132-137 can contain various fluids used in an automated staining process for a sample under analysis. In particular embodiments, reservoir 132 may comprise a protein blocking buffer, reservoir 133 may comprise a wash solution, reservoir 134 may comprise an imaging solution, reservoir 135 may comprise a cleavage solution, reservoir 136 may comprise biotin, and reservoir 137 may comprise an avidin blocking buffer.

Imaging system 110 comprises a microscope 101, as well as an imaging light source 140 configured to image a sample in sample chamber 120. In the embodiment shown, light source 140 is coupled to a light guide adapter 148, liquid light guide 147, and a TTL shutter control 105. In particular embodiments, imaging light source 140 is a solid state light engine. In the illustrated embodiment, microscope 101 comprises a base 115, a motorized stage 111, a stage controller 112, a camera 113, an objective 107, a motorized nosepiece 109. In particular embodiments, imaging system 110 may also comprise a motorized filter turret, filter block and filter cube (not labeled in the figures for purposes of clarity).

In the embodiment shown, apparatus 100 can be controlled via a remote control unit 114. Apparatus 100 further includes a multifunction data acquisition (DAQ) device 116, a frame grabber 118, a computer 117 and a serial USB hub 119 in this embodiment. In the embodiment shown, apparatus 100 also comprises a cooling element 145 for sample chamber 120. In particular embodiments, cooling element 145 may comprise a temperature control block (e.g., a Peltier unit) and a liquid cooler.

Figure 14:
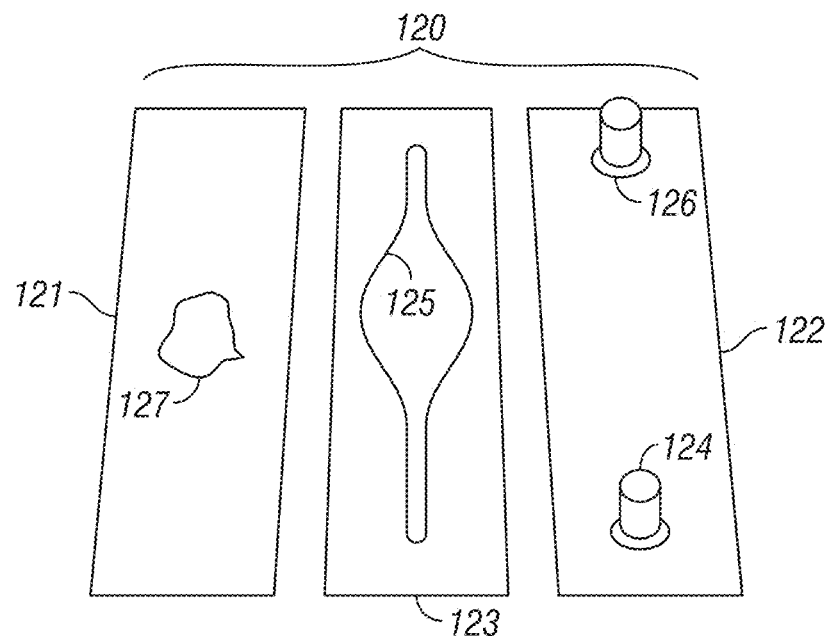
FIG. 14. Exploded view of a sample chamber according to exemplary embodiments disclosed herein.
Figure 15:
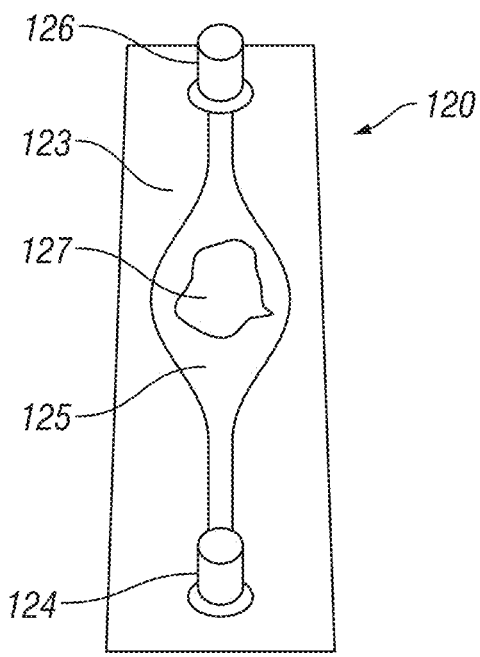
FIG. 15. Assembly view of the sample chamber of FIG. 14.

Referring now to FIGS. 14 and 15, respectively, an exploded view and assembled view of one embodiment of sample chamber 120 is provided. In this embodiment, sample chamber comprises a microscope slide 121, a coverslip 122, and a gasket 123 disposed between microscope slide 121 and coverslip 122. The embodiment shown also comprises a fluid inlet 124 and a fluid outlet 126 coupled to coverslip 122. Gasket 123 comprises an open portion 125 positioned in the interior of gasket 123, such that gasket 123 surrounds open portion 125. In this embodiment, open portion 125 comprises a central volume and extended portions in fluid communication with fluid inlet 124 and fluid outlet 126. In the assembled view of FIG. 15, a sample 127 is located in open portion 125 and between microscope slide 121 and coverslip 122. Accordingly, sample 127 is contained within sample chamber 120, and fluid inlet 124 and fluid outlet 126 can provide for fluid flow into sample chamber 120.

Referring back now to FIG. 13, fluid inlet 124 and fluid outlet 126 are each coupled to an optical bubble sensor 142 and 146, respectively. Fluid inlet 124 is also coupled to and in fluid communication with valves 141 and 143, as well as reservoirs 138 and 139 (which can contain an antibody solution and a PCL solution, respectively). In certain embodiments, valves 141 and 142 may be configured as solenoid valves. Fluid outlet 126 is also coupled to valve 151 and a fluid transport device 150, which in certain embodiments may be configured as a syringe pump. Valve 151 is also coupled to waste reservoir 152. During operation, the flow of fluids from reservoirs 132-137 can be controlled (e.g., via operation of valves 131, 141 and 143) to fluid inlet 124 to provide automated labeling and staining of sample 127 according to the methods disclosed herein.

Figure 16:
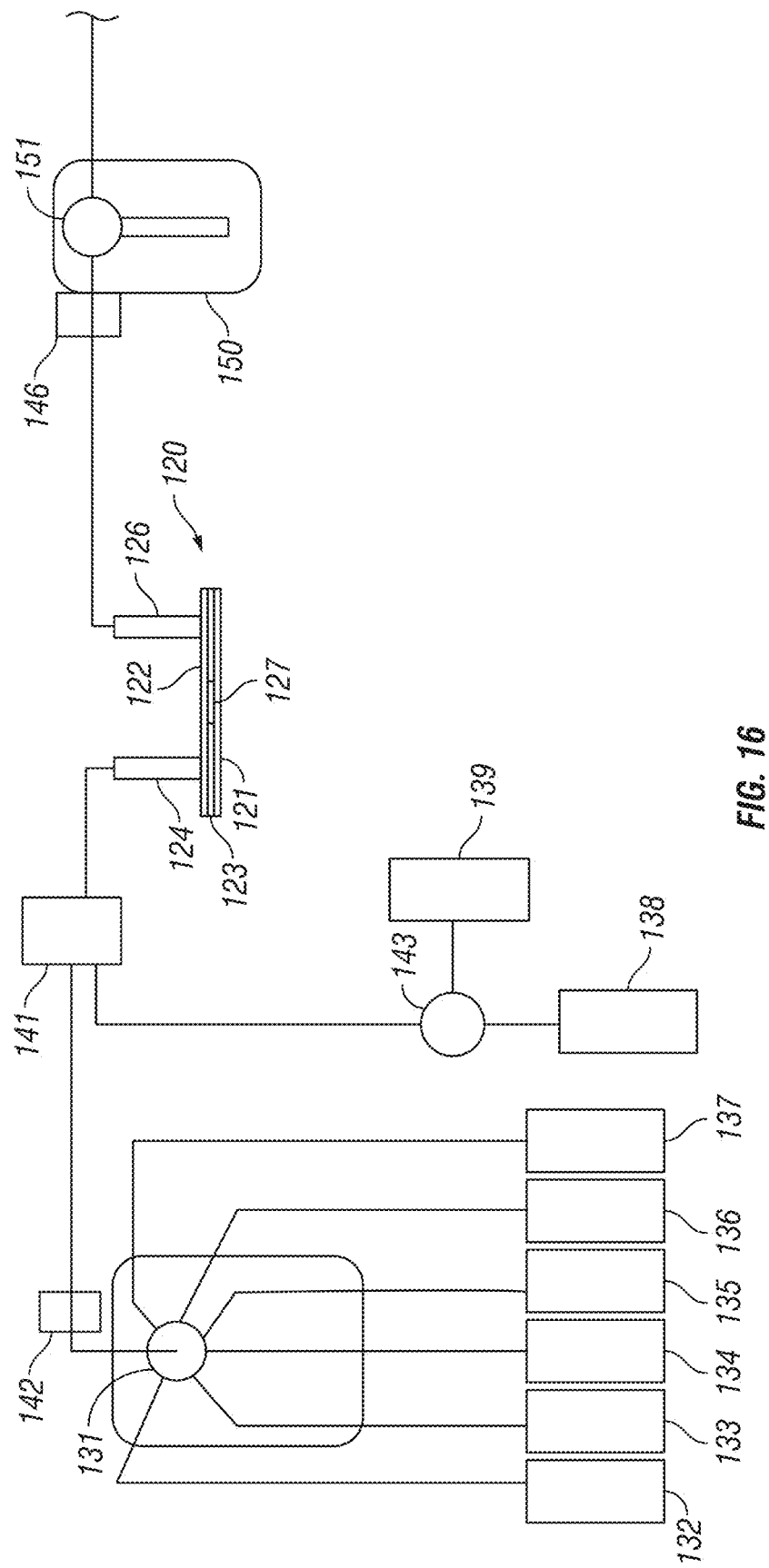
FIG. 16. Schematic of a portion of the apparatus of FIG. 13 including a fluid control system and sample chamber.

FIG. 16 provides a partial schematic diagram of fluid control system 130 and sample chamber 120. As shown in this embodiment, gasket 123 is located between microscope slide 121 and coverslip 122. Fluid inlet 124 and fluid outlet 126 are in fluid communication with components of fluid control system 130 that allows for automated serial staining of sample 127. For example, fluid control system 130 can provide for the transfer of fluids from reservoirs 132-139 to sample chamber 120 in order to perform the steps disclosed in the methods described herein.

Figure 17:
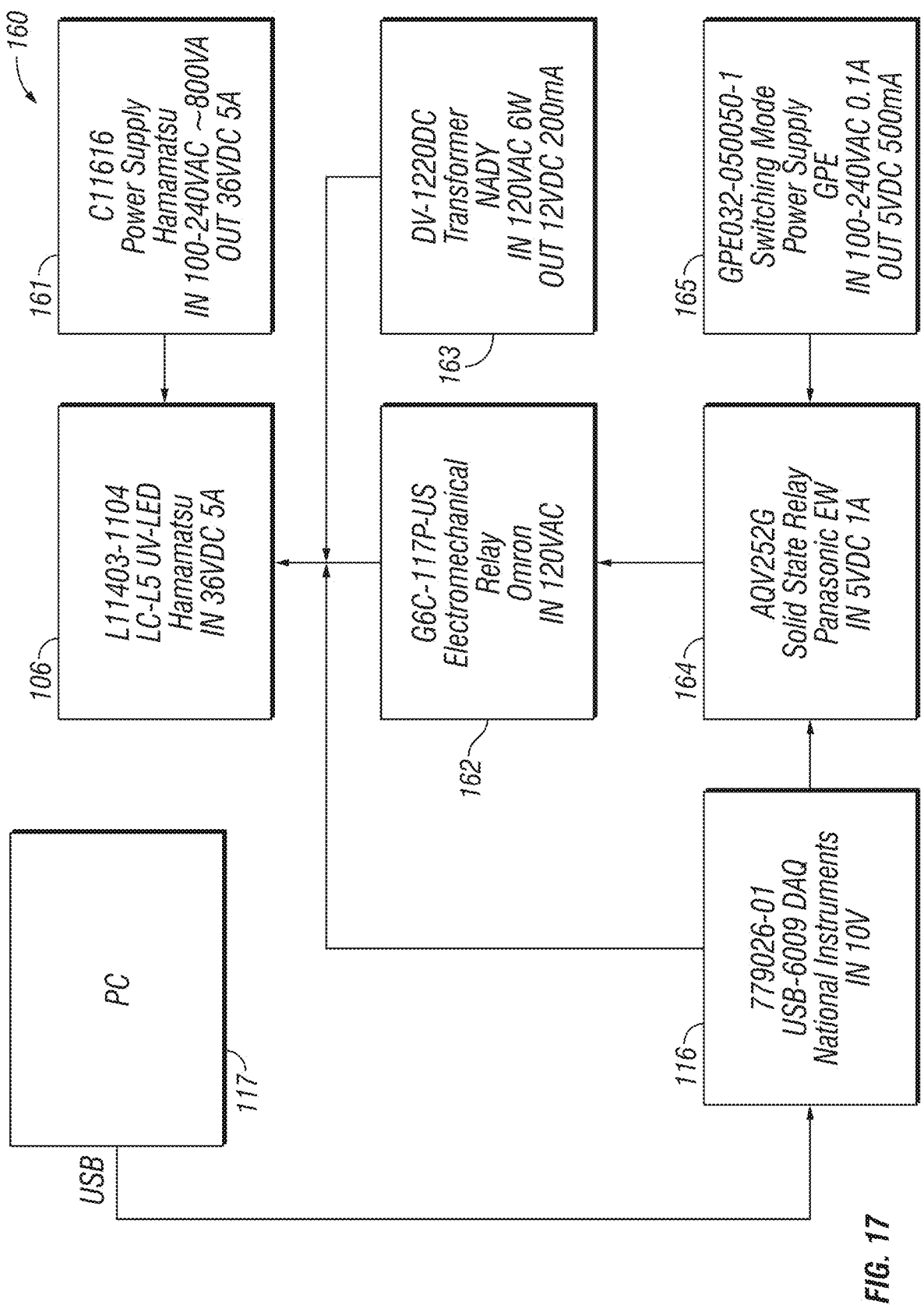
FIG. 17. Schematic of a portion of the apparatus of FIG. 13 including a power and control system.
Figure 18:
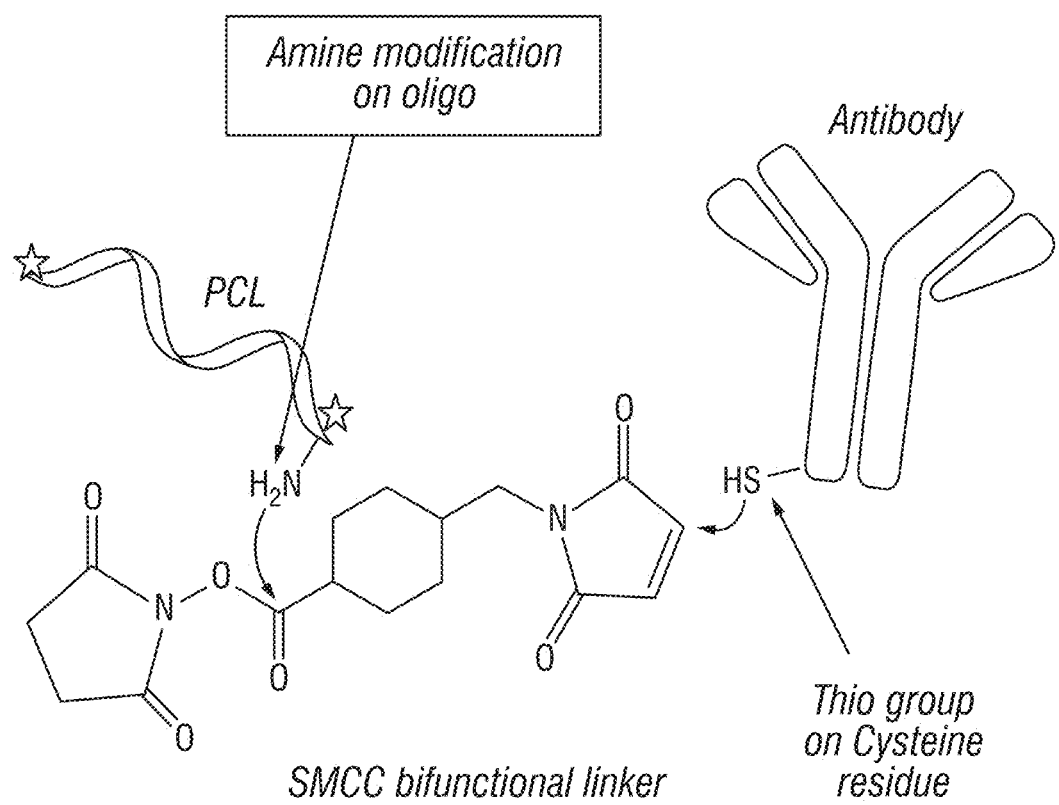
FIG. 18. Exemplary modified oligo with an SMCC (Succinimidyl-4-[N-maleimidomethyl]cyclohexane-1-carboxylate) bifunctional crosslinker.
Figure 19A:
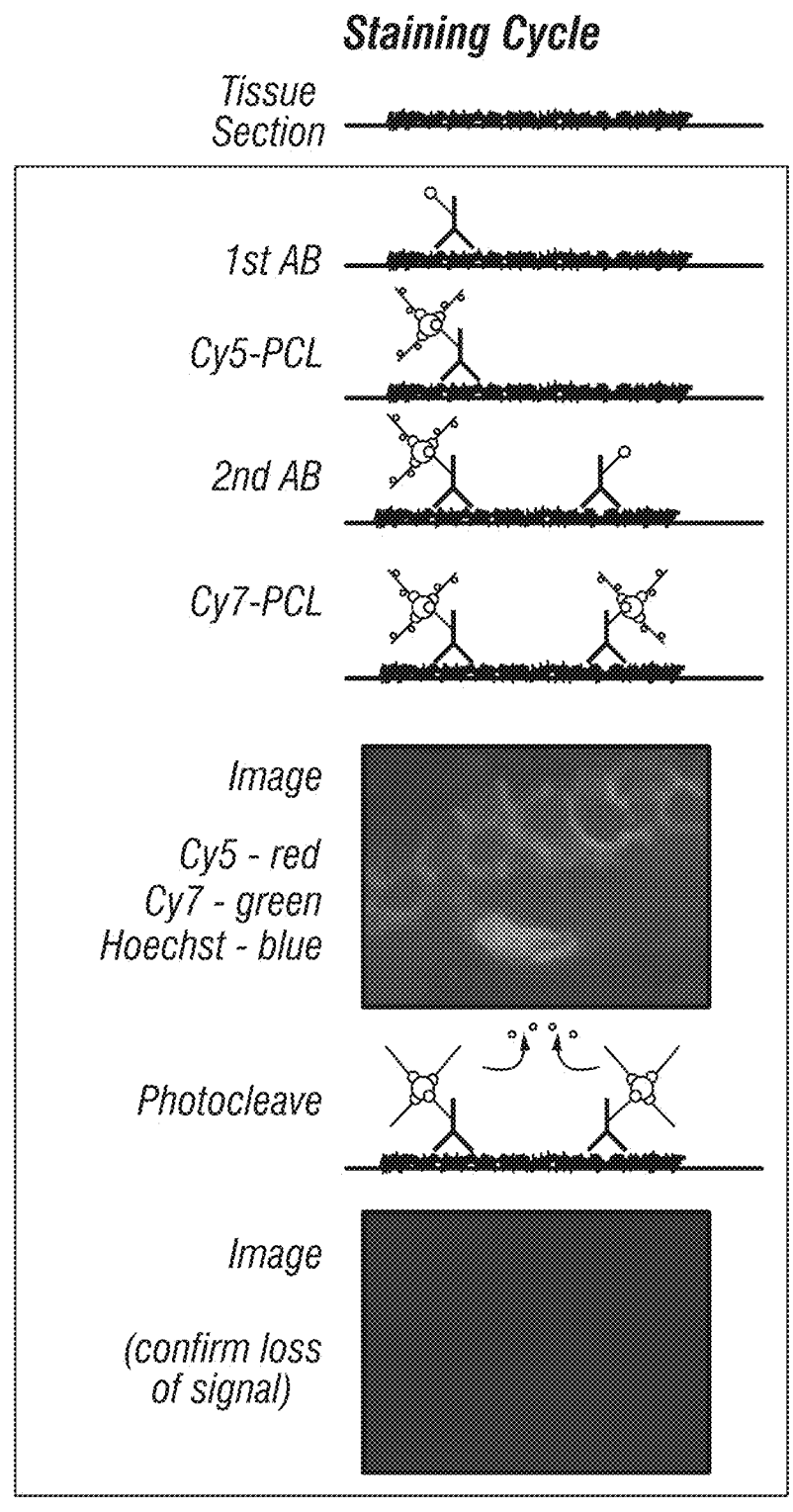
FIGS. 19A-E.
Figure 19B:
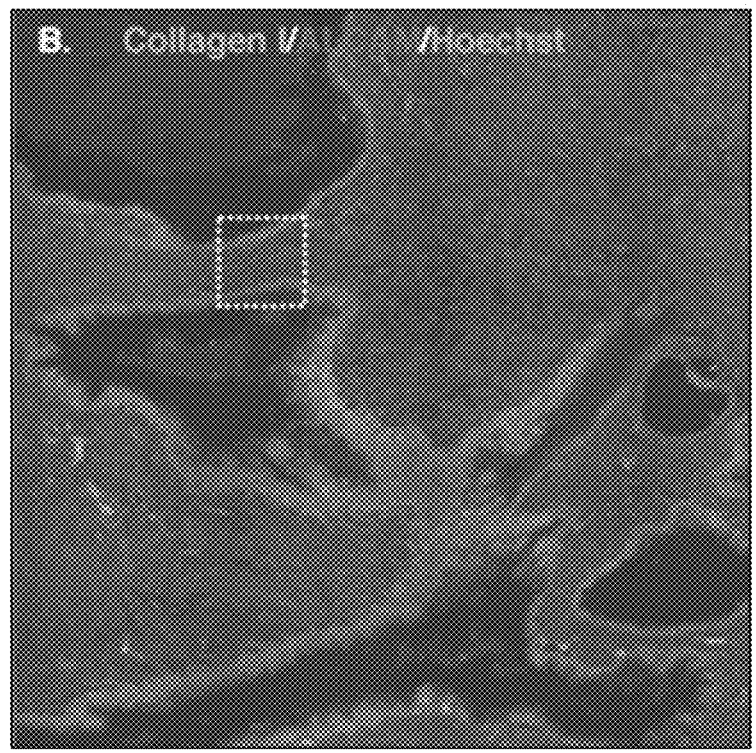
Figure 19C:
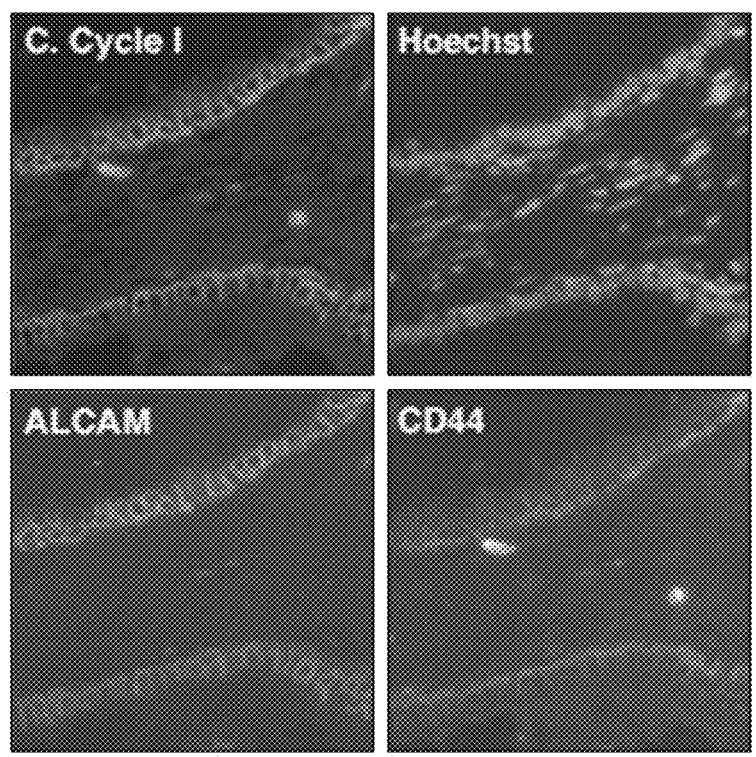
Figure 19D:
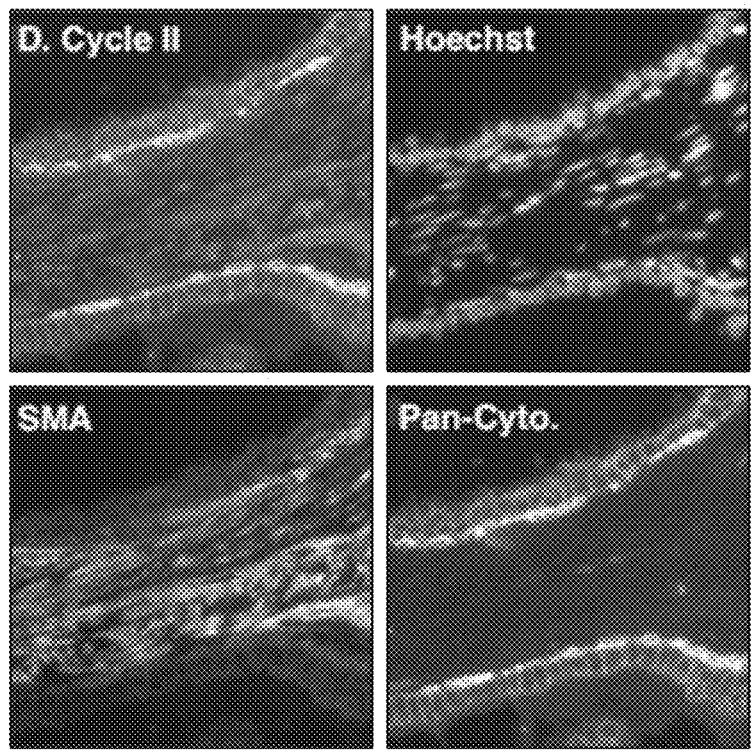
Figure 19E:
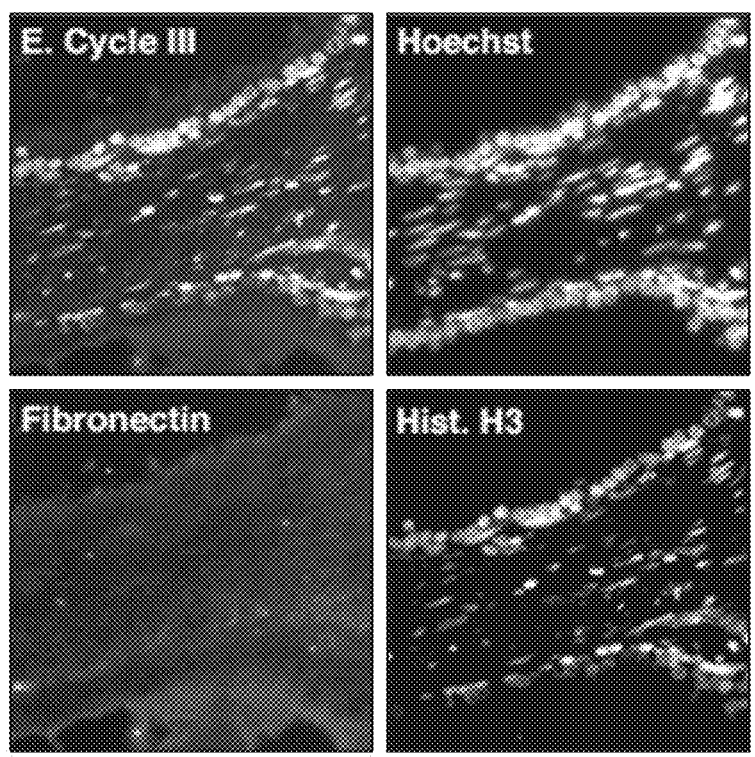

FIG. 17 provides a schematic diagram of one exemplary embodiment of a power and control system 160 for a light source 106 configured to photocleave an antigen-binding complex from an antigen on or in a sample in sample chamber 120. In particular embodiments, light source 106 can be configured as an LED head unit. It is understood that the component model numbers indicated in FIG. 16 are merely exemplary of one embodiment, and that other embodiments of exemplary systems may comprise different components and model numbers.

In the embodiment shown in FIG. 17, system 160 is an ultra-violet (UV) reverse termination sub-system in which LED head unit 106 is a Hamamatsu LC-L5 UV LED array configured to provide excitation at 365 nm for cleavage of the PCL. In this embodiment, system 160 is controlled by computer 117 via LabView software through multifunction data acquisition (DAQ) device 116 providing a digital output line to turn LED head unit 106 on and off as well as an analog output line to set the UV intensity via a 0-10 V signal. A solid state relay 164 coupled with an electromechanical relay 162 switch a 12 VDC signal from a 120 VAC-12 VDC transformer 163 to turn the UV LED array in LED head unit 106 on and off. A 5 VDC switching mode power supply 165 provides power to solid state relay 164. LED head unit 106 gets power from its own 36 VDC power supply 161.

IV. DEFINITIONS

The term "antigen" as used herein refers to any target material present on or in a sample. For example, the antigen may be a protein, a sugar, a lipid, a nucleic acid, a ligand, a carbohydrate, a drug target, or a combination thereof. The antigen may be present in or on a cell. The antigen may be present only in or on a cancerous cell but not a normal cell. The antigen may be present in a cell-free sample, such as serum or a cell lysate.

The term "sample" as used herein refers to any biological sample in which an antigen may be present. For example, the sample may be a biopsy sample, tissue sample, cell suspension, cell culture, or a combination thereof. Further, the sample may be isolated from an animal, such as a primate (e.g., human), mouse, rat, guinea pig, hamster, rabbit, cat, dog, pig, cow, or horse. In some cases, the sample may be a plant sample, a bacterial sample, or a fungal sample. The sample may be an animal body fluid such as, for example, blood, bone marrow fluid, lymph, saliva, lachrymal fluid, urine, mucosal fluid, amniotic fluid, or a combination thereof. The sample may be a cell mixture including different types of cells mixed therein. The mixture may include cells having the antigen and cells that do not. The sample may comprise circulating tumor cells (CTCs), cancer stem cells, immune cells, fetal stem cells, fetal cells, cancer cells, tumor cells, and/or normal cells.

The term "antigen-binding complex" as used herein refers to any complex that comprises a component that is capable of selectively or specifically binding to an antigen. An antigen-binding complex will also comprise a component to which a photocleavable label is covalently bound, which component may be the same as or different than the component that binds to the antigen. The component that is capable of selectively or specifically binding to an antigen may be, without limitation, a primary antibody; an aptamer; a ligand for a receptor where the receptor is the antigen; a receptor for a ligand where the ligand is the antigen; a substrate, inhibitor, or cofactor for an enzyme where the enzyme is the antigen; a drug molecule where the drug target is the antigen; a lectin where a carbohydrate is the antigen; an RNA molecule where an at least partially complementary nucleic acid (e.g., DNA or RNA) is the antigen; a DNA molecule where an at least partially complementary nucleic acid (e.g., DNA or RNA) is the antigen; etc. Additional examples include use of Annexin A5 to specifically bind to phosphatidylserine on a cell surface, use of lectins to specifically bind to carbohydrate moieties, use of a nuclear receptor that specifically binds to a hormone ligand and the antigen is either the hormone ligand or a DNA regulatory element bound by the nuclear receptor in the presence of the hormone ligand.

The term "primary antibody" as used herein generally refers to the component in an antigen-binding complex that selectively or specifically binds the antigen. A primary antibody may be, for example, an antibody, an antibody mimetic, an aptamer, a receptor, a ligand, an enzyme substrate, an enzyme inhibitor, an enzyme cofactor, or an enzyme.

The term "antibody mimetic" as used herein refers to organic compounds (including artificial peptides or proteins with a molar mass of about 3 to 20 kDa, nucleic acids, and small molecules) that, like antibodies, can specifically bind antigens, but that are not structurally related to antibodies. Examples of antibody mimetics include, without limitation, affibody molecules, affilins, affimers, affitins, alphabodies, anticalins, avimers, DARPins, fynomers, Kunitz domain peptides, and monobodies.

The term "aptamer" as used herein refers to oligonucleotide or peptide molecules that bind to a specific target molecule, e.g., an antigen. Some aptamers are single-stranded nucleic acids that fold into a well-defined three-dimensional structure. Aptamers show a high affinity and specificity for their target molecules and in some cases inhibit their biological functions. Aptamers can be created by selecting them from a large random sequence pool. Natural aptamers also exist in the form of riboswitches, which can be used to selectively or specifically detect a ligand antigen. In the case of oligonucleotide-based aptamers, the photocleavable label may be covalently bound directly to the aptamer itself, thus producing a single component antigen-binding complex.

The term "secondary antibody" as used herein refers to antibodies of any immunoglobulin class that specifically bind to the Fc portion of a primary antibody. The Fc portion of an immunoglobulin (Ig) monomer corresponds to the stem of the Y-shaped Ig molecule and consists of the C-terminal sections of the two heavy chains linked by one or more disulfide bonds.

The term "first ligand" as used herein refers to any molecule that can be covalently bound to a component (e.g., a primary antibody, a secondary antibody, etc.) of an antigen-binding complex. One example of a first ligand is biotin. Biotin is a vitamin present in all living cells that binds with high affinity to avidin or streptavidin. The binding between biotin and avidin/streptavidin is the strongest ($K_a=10^{15}$ $M^{-1}$) known non-covalent interaction between a protein and ligand. Since biotin is a relatively small molecule, it can be conjugated to proteins (e.g., antibodies) without altering their biological activity. Furthermore, a single protein (e.g., antibody) may be conjugated to several occurrences of biotin that can each then bind a molecule of avidin. Biotin occurs naturally; thus, surface blocking of non-specific binding of biotin or avidin/streptavidin is required when biotin-avidin/streptavidin systems are used. A commonly used two-step blocking strategy includes: incubation with an excess of avidin/streptavidin to block endogenous biotin-rich enzymes and then incubation with an excess of biotin to block in the introduced avidin/streptavidin. Another example of a first ligand is an oligonucleotide. Such an oligonucleotide may be covalently bound to a component (e.g., a primary antibody, a secondary antibody, etc.) of an antigen-binding complex. Such an oligonucleotide may be single stranded. Such an oligonucleotide may be comprised of ribonucleic acids, deoxyribonucleic acids, or derivatives thereof. Such an oligonucleotide may be at least 10, 11, 12, 13, 14, 15, 16, 17, 18, 19, 20, 25, 30, 35, 40, 45, 50, 55, 60, 65, 70, 75, 80, 85, 90, 95, or 100 nucleotides long.

The term "first anti-ligand" as used herein refers to any molecule that can specifically and/or selectively bind to the first ligand. For example, if the first ligand is biotin, then the first anti-ligand may be avidin. The term "avidin" as used herein generically refers to any biotin-binding protein, including both natural proteins and recombinant and genetically engineered proteins. The term includes the two common biotin-binding proteins known as "egg white or avian avidin" and "streptavidin." Egg white or avian avidin, commonly referred to simply as avidin, is a protein that is a constituent of egg white and forms a non-covalent complex with biotin. Streptavidin is a protein isolated from the actino-bacterium *Streptomyces avidinii* and also forms a non-covalent complex with biotin. Other bacterial sources of biotin binding proteins are also known. Both egg white avidin and streptavidin are tetrameric proteins in which the biotin binding sites are arranged in pairs on opposite faces of the avidin molecule. Accordingly, both of the above avidins have the ability to bind to up to four molecules of biotin, either in the free form or in a derivative form and, thereby, form a "complex." A derivative form of biotin results from the conjugation of biotin to another molecule. As another example, if the first ligand is an oligonucleotide, then the first anti-ligand may be a second oligonucleotide that is at least partially complementary to the first ligand.

The term "second ligand" as used herein refers to any molecule that can specifically and/or selectively bind to the first anti-ligand. For example, if the first ligand is biotin and the first anti-ligand is avidin, then the second ligand may be biotin.

The term "functional linker" as used herein refers to any molecule that can be covalently bound by a photocleavable label and a component of an antigen-binding complex (e.g., a first ligand, a first anti-ligand, a second ligand, a primary antibody, a secondary antibody, or an aptamer). The functional linker may be a nucleic acid. Such a nucleic acid may be at least two, three, four, five, six, seven, eight, nine, 10, 11, 12, 13, 14, 15, 16, 17, 18, 19, 20, 25, 30, 35, 40, 45, 50, 55, 60, 65, 70, 75, 80, 85, 90, 95, or 100 nucleotides long. Such a nucleic acid may be single stranded, double stranded, or partially double stranded. The functional linker may be a peptide. The functional linker may be a fatty acid chain. The functional linker may be photo-stable.

As used herein, "essentially free," in the context of a specified component, means that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred are compositions in which no amount of the specified component can be detected with standard analytical methods.

The use of the word "a" or "an," when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended.

For example, any method that "comprises," "has" or "includes" one or more steps is not limited to possessing only those one or more steps and also covers other unlisted steps.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 8:
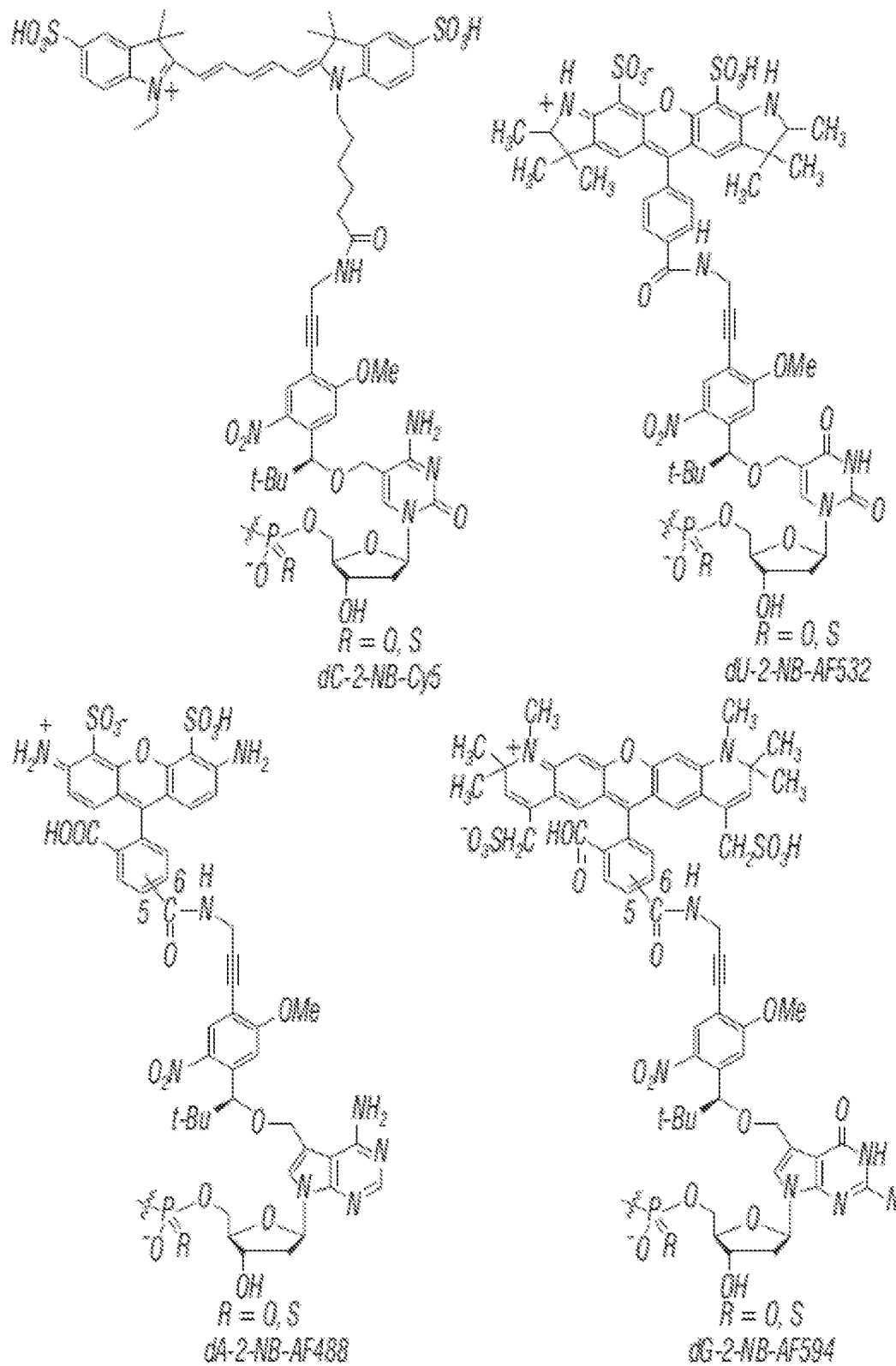
FIG. 8. Exemplary nucleotide-photocleavable moiety-fluorescent dye structures, such as those illustrated in FIGS. 2 and 4-6.

Detection of an Antigen in a Tissue Section Using Single-Stranded Biotin-Nucleotide-Fluorophore Tags This Example illustrates an antigen-bound antigen-binding complex of formula (IX). First, formalin-fixed paraffin embedded (FFPE) prostate cancer tissue sections were prepared and blocked with BSA in PBS. Then, the sections were incubated with a mouse anti-cytokeratin antibody, followed by washing. Next, the sections were incubated with biotinylated goat anti-mouse IgG secondary antibody, followed by washing. Then, the sections were incubated with either avidin or streptavidin or buffer alone, followed by washing. Then, the sections were incubated with either a biotin-conjugated photocleavable Cy5 or avidin-fluorescein, followed by washing. The biotin-conjugated photocleavable Cy5 had a biotin modification at its 5' end and a dC-Cy5 (FIG. 8) at its 3' end. Finally, the sections were imaged using a 20× water immersion lens. FIG. 1 shows that the biotin-conjugated photocleavable Cy5 produced a signal in a manner dependent on the biotinylation of the secondary antibody.

Figures 9D, 9E:
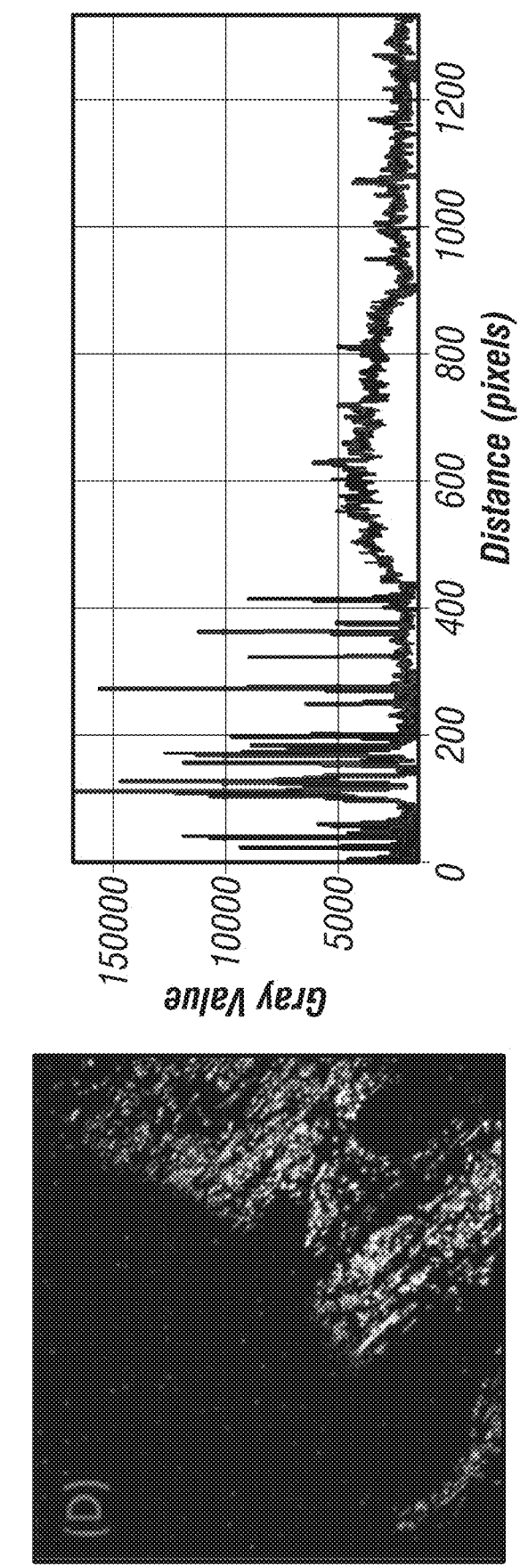

In another experiment, sections of a formalin-fixed paraffin embedded human prostate were incubated with biotinylated anti-smooth muscle actin. Then, the sections were incubated sequentially with avidin or streptavidin and a biotin-conjugated probe containing photocleavable Cy5. In this instance, an automated fluid exchange program was used in coordination with the probe, which consisted of a double stranded nucleotide linking two opposing biotins. The Cy5 was incorporated into the nucleotide backbone. Unbound probe was washed and the tissue was imaged prior to and after photocleavage. After the slide was imaged with a fluorescent microscope with Cy5, a single location in the tissue was photocleaved using a 2 min UV exposure and re-imaged in a pre-programmed manner. FIG. 9A shows an image of the stained section prior to cleavage while FIG. 9B shows the same area after photocleavage. The section was imaged again following a buffer wash (FIG. 9C). FIG. 9E shows the image pixel intensity profile along the line in FIGS. 9A-C, illustrating the image brightness change after cleavage and wash. FIG. 9D shows a different field-of-view following cleavage and illustrates the cleavage boundary (the upper-left corner was exposed to UV light).

Example 2

Figure 11:
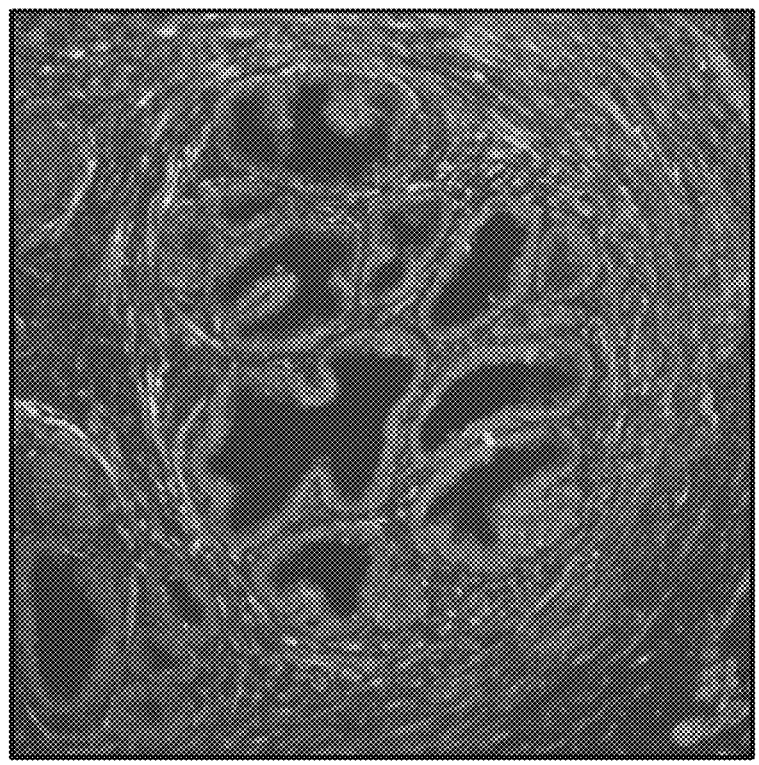
FIG. 11. Serial tissue staining. FFPE tissue staining of two target proteins with two photocleavable labels of different colors. The same field of view was imaged in the first color and overlaid on the previous color with ImageJ software.

Automated Serial FFPE Tissue Staining of Two Target Proteins with Two Photocleavable Labels of Different Colors This Example illustrates an antigen-bound antigen-binding complex of formula (VII). For serial FFPE, the tissue was first incubated with biotinylated anti-smooth muscle actin for 2 h, avidin for 30 min, and biotin-conjugated probe containing photocleavable AF532 for 20 min before the green channel was imaged. After UV exposure of 2 min at 150 mW/cm$^2$, the tissue underwent the same staining procedure with histone H3 antibody and red photocleavable Cy5. The same field of view was imaged in the red channel and overlaid on the previous green channel using ImageJ software (FIG. 11).

Direct comparison of PCL with chemical inactivation and photobleaching of Cy dyes demonstrates the release of dye from PCL is 10-100 times more rapid. A similar comparison with other photocleavable bonds demonstrated that the PCL resulted in faster and more complete dye release than other photocleavable reactions.

An automated NGH platform for FFPE tissue sections was developed and designed to use a photocleavable fluorophore that is released within seconds using UV irradiation. This unique photocleavable label enables rapid cycles of repeated staining in the same tissue section without the need to remove the antigen-detecting antibody. The NGH platform also includes automated fluidics for reduced hands-on time and a four-color epi-fluorescence microscopy imaging system for multiplex reporter detection.

FFPE tissue sections were mounted onto standard glass slides, heat-fixed, dewaxed, hydrated, and placed in a specialized flowcell. Using automated fluidics, the tissue was blocked, washed, and exposed to biotinylated primary antibody using standard reagents. Antibody binding was detected using avidin or streptavidin-photocleavable label complexes, which were imaged prior to the label being photocleaved in preparation for the next staining cycle.

The NGH approach enabled serial staining of prostate tissue sections. This staining strategy enabled rapid imaging of antigens.

Example 3

Multiplex Staining of 8 Target Regions on a Single FFPE Tissue Section with Two Color Photocleavable Labels In another experiment, a 6 μm section of human prostate (normal) was prepared and stained in three consecutive cycles. Tissue section was probed for multiple target proteins at each cycle, a single imaging event at each cycle at various wavelengths captured signal from various target proteins. Following a cleaving event through UV exposure, the tissue was probed again for the next set of target proteins. Three such multiplex cycles resulted in capture of the following 8 targets in a single tissue section: Cycle I: Collagen (CNA35), Hoechst (nuclear DNA), anti-ALCAM and anti-CD44; Cycle II: anti-cytokeratin and anti-SMA;

Cycle III: anti-Fibronectin and anti-Histone H3. Each cycle captured images from four channels: Cy7 (750 nm), Cy5 (650 nm), Cy2 (488 nm) and Hoechst (365 nm). At the completion of the experiment, the three image data sets were co-registered using the Cy2 channel. Image integration into a single 12-channel image was performed using ImageJ software. FIG. 19 shows the cyclic multiplex staining and imaging.

Cyclic multiplex staining successfully achieved immunofluorescent detention with six distinct antibodies in addition to two non-antibody stains (collagen and nuclear stains) over three cycles of staining. There was no visible deterioration or deformation of the tissue during the procedure and there was no significant accumulation of non-specific signal across the cycles when comparing the baseline images (capture before cycle I) and the images after photo cleaving (captured after cycle I, II, and III).

Example 4

Figure 20:
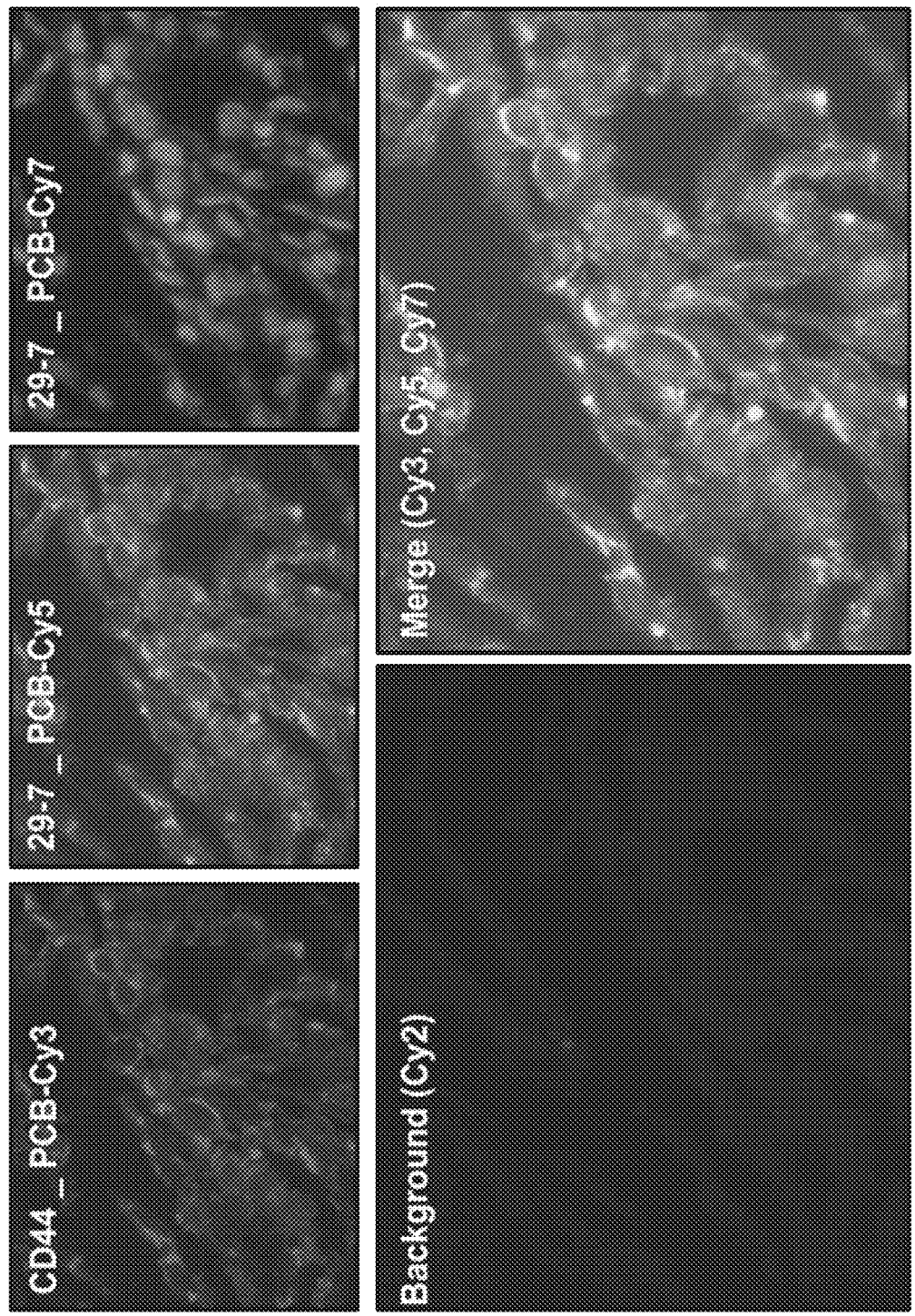
FIG. 20. Image of an FFPE tissue section with multiplex staining using three color photocleavable labels simultaneously. Images captured signal at the three appropriate wavelengths for Cy3, Cy5, and Cy7, then image merging was performed using ImageJ software to co-visualize the three distinct regions.
Figure 21B:
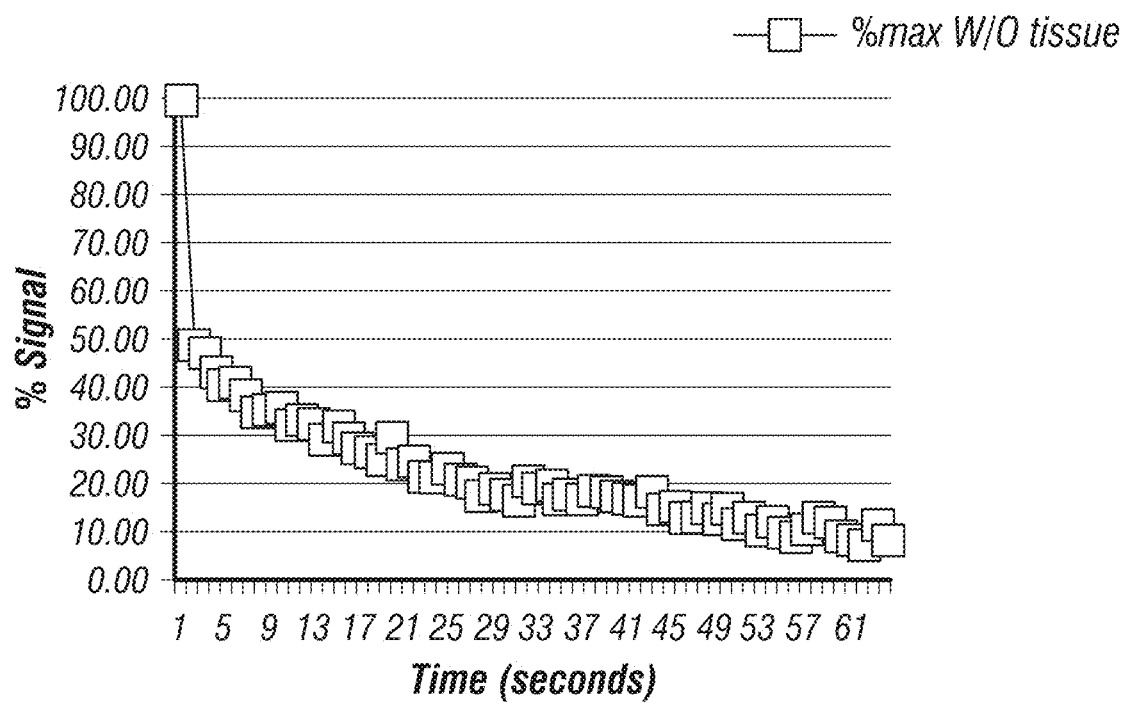
Figure 21C:
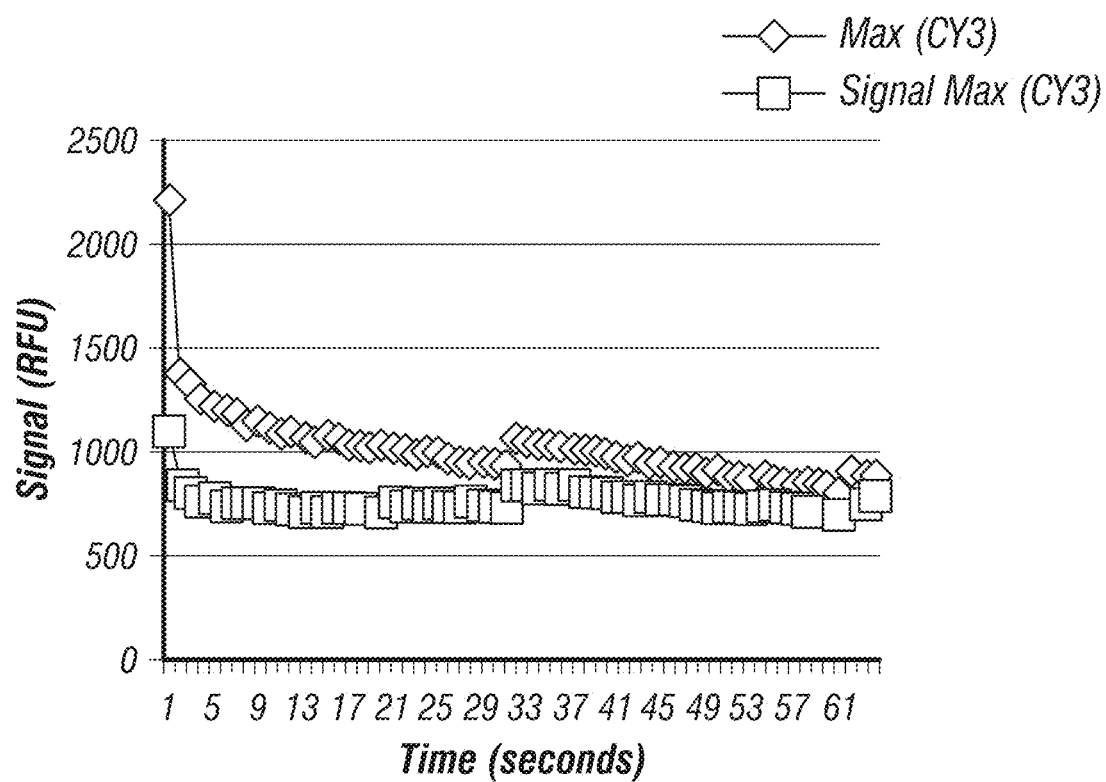

Multiplex Staining of FFPE Tissue Section with Three Color Photocleavable Labels FFPE tissue section was prepared using procedures described in Example 2. Multiplex staining was achieved on three tissue regions on the same tissue section using three antibodies with three unique biotin-photocleavable labels, each with a unique fluorescent dye. The tissue section was blocked, and sequentially incubated with biotin-labeled primary antibody, streptavidin, biotin-labeled photocleavable label, and this cycle was repeated for the subsequent two antibodies and photocleavable labels. Anti-CD44 was detected by photocleavable Cy3, anti-29-7 by photocleavable Cy5, and anti-Histone H3 by photocleavable Cy7. A single image captured signal at the three appropriate wavelengths, and image merging was performed using ImageJ software to co-visualize the three distinct regions in three distinct colors (FIG. 20). A single photocleaving event released signal from all photocleavable labels, post-imaging (FIG. 21).

Example 5

Detection of an Antigen in a Tissue Section Using Partially Double-Stranded Biotin-Nucleotide-Fluorophore Tags To prepare partially double-stranded biotin-oligonucleotide-photocleavable Cy5 fluorescent dye, dC-Cy5 (FIG. 8) was extended to 3' of the top oligo using DNA polymerase as shown in FIG. 2. The duplex product was purified by RP-HPLC. The volume of the collected duplex product solution was reduced. Then, the product was diluted to 50 µM final concentration in 1×PBS.

The partially double-stranded oligonucleotide-photocleavable Cy5 fluorescent dye was used in an experiment as described in Example 1 and compared to the results obtained using a single stranded oligo. Both designs of the photocleavable label performed well.

Example 6

Evaluation of Staining and Photocleavage with Various PCLs

Figure 10A:
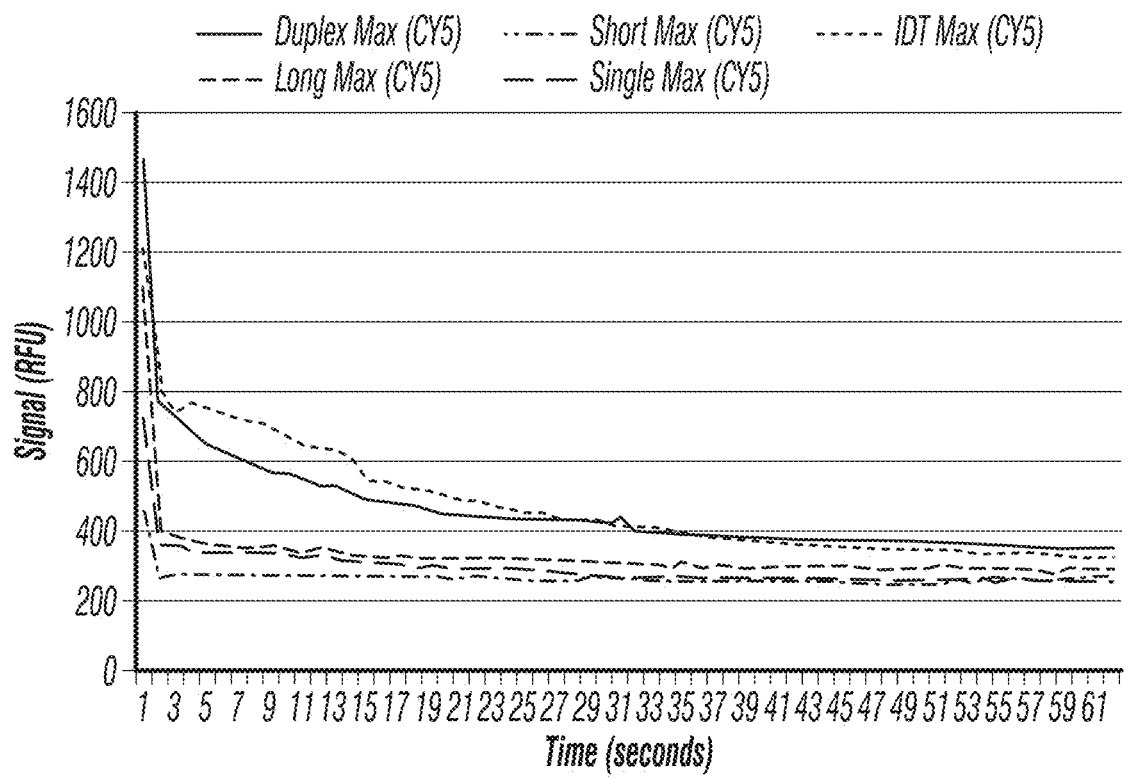
Figure 10B:
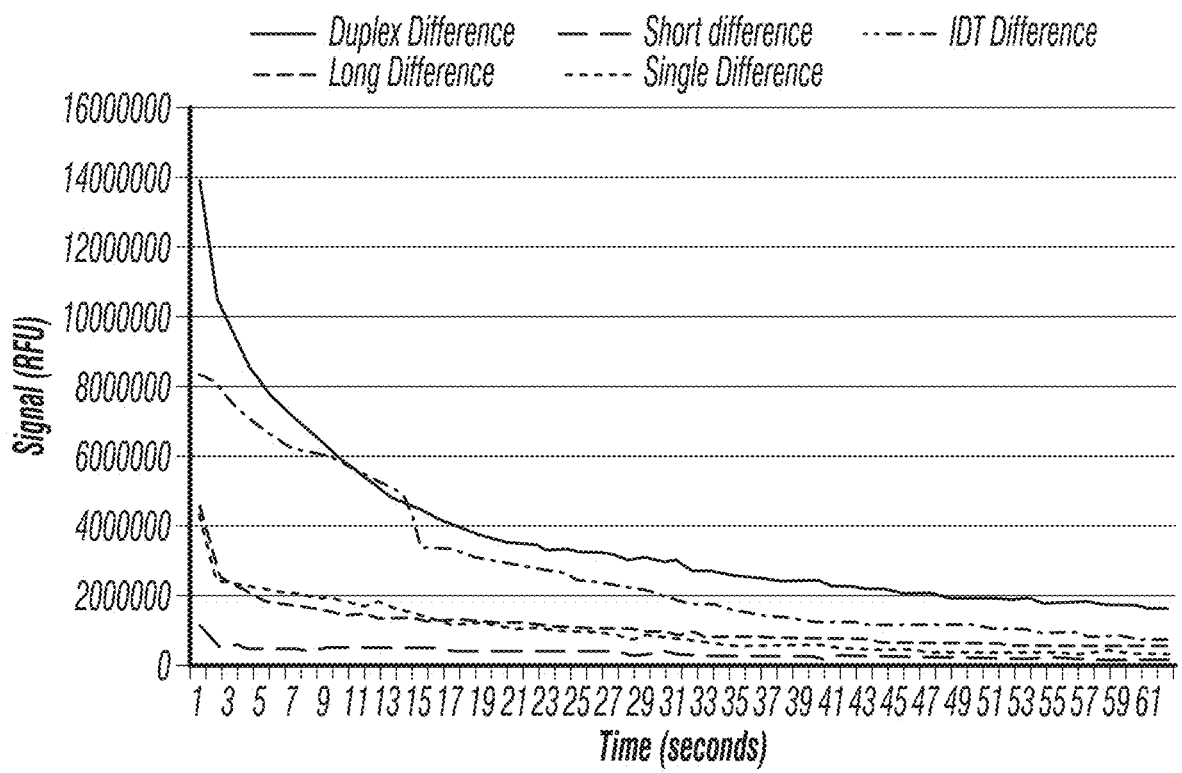
Figure 10C:
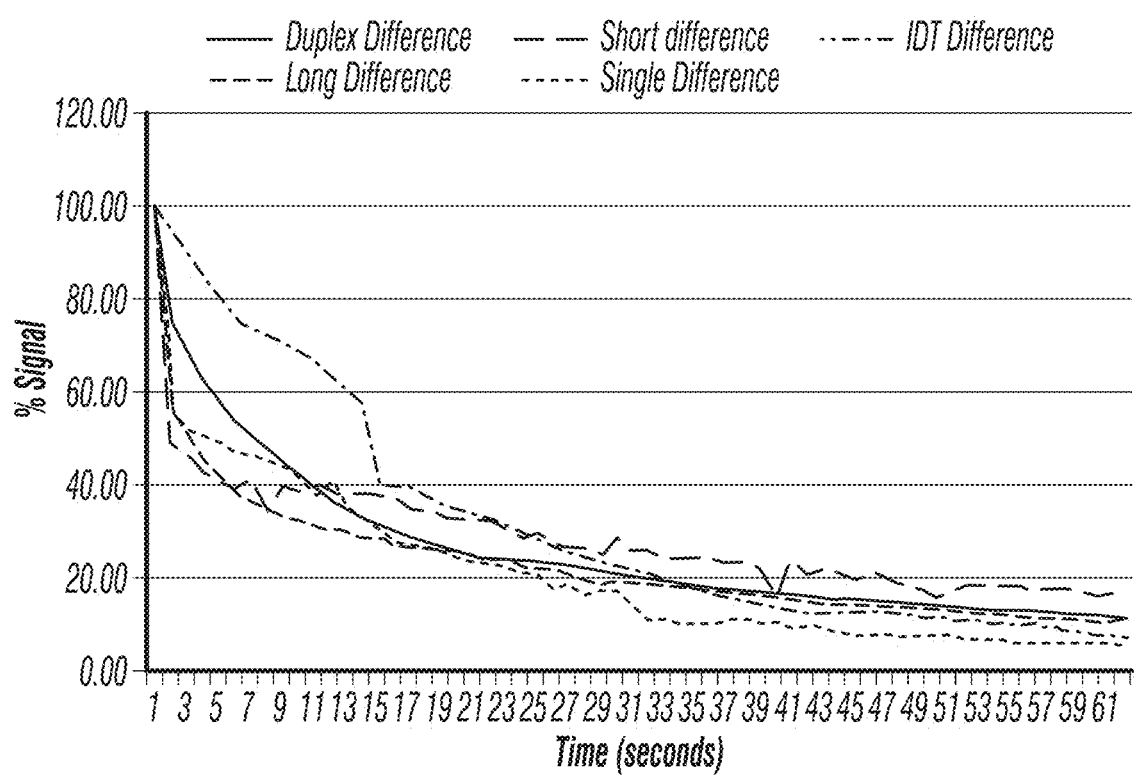
Figure 10H:
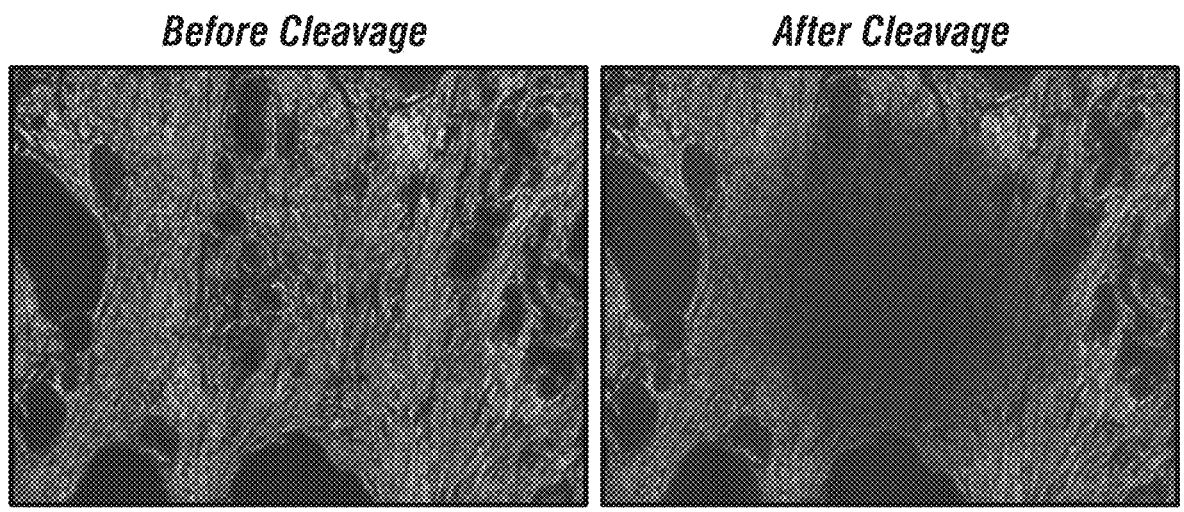
Figure 12:
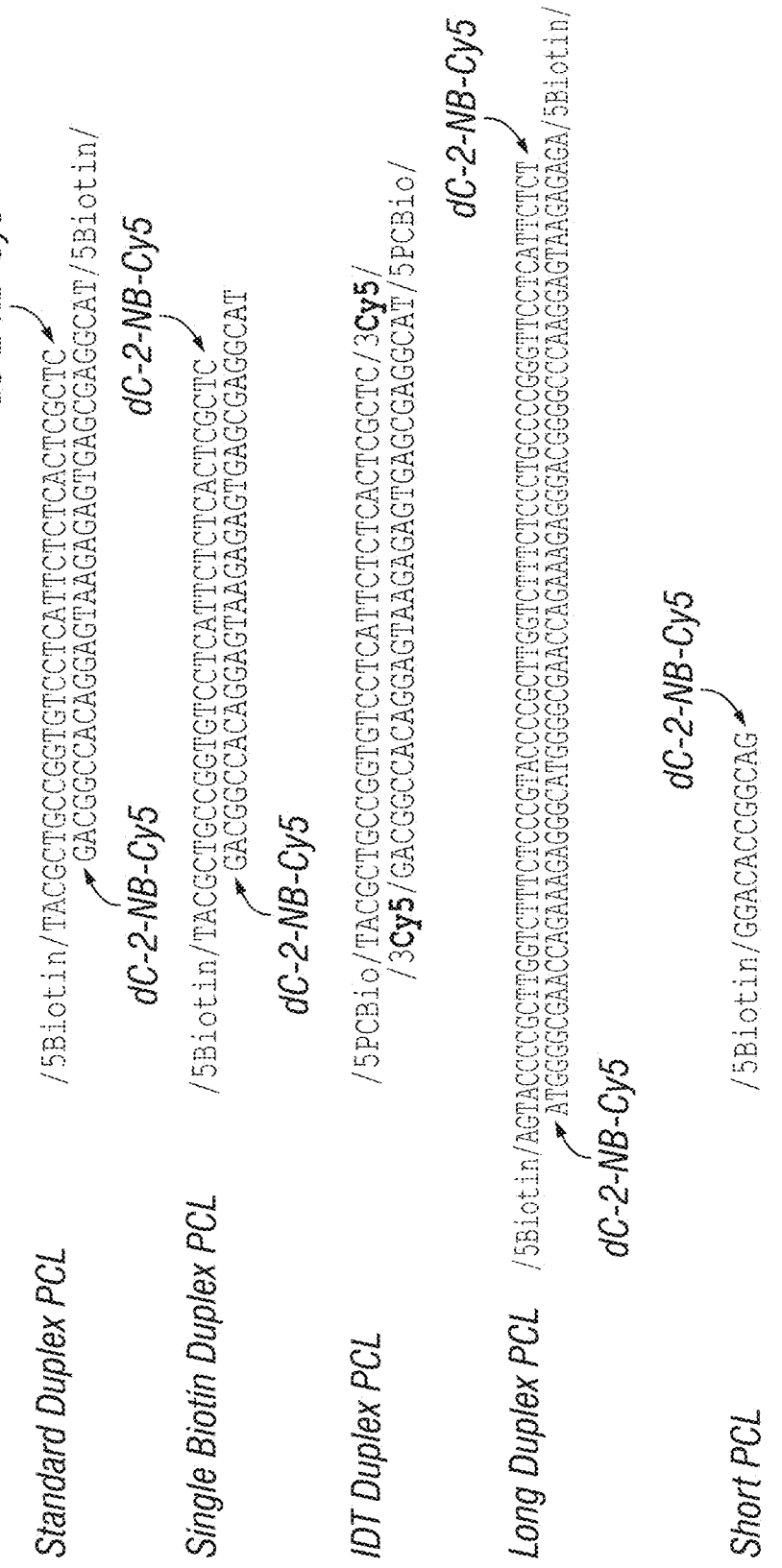
FIG. 12. Illustration of the photocleavable labels used in Example 5. The Standard Duplex PCL consisted of two 34-nucleotide oligos having a biotin on their 5' ends and a photocleavable fluorescent label on their 3' ends, the oligos were annealed to form a 28-nucleotide double-stranded section with four nucleotide single-stranded overhangs on each end. The sequence of the top strand of the Standard Duplex PCL is provided as SEQ ID NO: 3; the sequence of the bottom strand of the Standard Duplex PCL is provided as SEQ ID NO: 4. The Long Duplex PCL consisted of two 69-nucleotide oligos having a biotin on their 5' ends and a photocleavable fluorescent label on their 3' ends, the oligos were annealed to form a 67-nucleotide double-stranded section with two nucleotide single-stranded overhangs on each end. The sequence of the top strand of the Long Duplex PCL is provided as SEQ ID NO: 15; the sequence of the bottom strand of the Long Duplex PCL is provided as SEQ ID NO: 16. The Short PCL consisted of a single 12-nucleotide oligo (SEQ ID NO: 17) having a biotin on its 5' end and a photocleavable fluorescent label on its 3' end. The Single Biotin Duplex PCL was the same as the Standard Duplex PCL except that only one of the two oligos in each hybrid had a biotin on its 5' end. The sequence of the top strand of the Single Biotin Duplex PCL is provided as SEQ ID NO: 3; the sequence of the bottom strand of the Single Biotin Duplex PCL is provided as SEQ ID NO: 4. The IDT Duplex PCL consisted of two 34-nucleotide oligos having a photocleavable biotin on their 5' ends and a fluorescent label on their 3' ends, the oligos were annealed to form a 28-nucleotide double-stranded section with four nucleotide single-stranded overhangs on each end. The sequence of the top strand of the IDT Duplex PCL is provided as SEQ ID NO: 3; the sequence of the bottom strand of the IDT Duplex PCL is provided as SEQ ID NO: 4.

Individual tissue sections (prostate cancer, human) were prepped in a single batch. Sections were blocked (avidin or streptavidin, biotin, total protein) and stained with biotinylated anti-SMA antibody followed by the addition of avidin, and then the addition of one of a series of PCLs (Standard Duplex PCL, Long Duplex PCL, Short Duplex PCL, and Single Biotin PCL; see FIG. 12) at identical concentrations. The Standard Duplex PCL consisted of two 34-nucleotide oligos having a biotin on their 5' end and a photocleavable fluorescent label on their 3' end, the oligos were annealed to form a 28-nucleotide double-stranded section with four nucleotide single-stranded overhangs on each end. The Long Duplex PCL consisted of two 69-nucleotide oligos having a biotin on their 5' end and a photocleavable fluorescent label on their 3' end, the oligos hybridized to form a 67-nucleotide double-stranded section with two nucleotide single-stranded overhangs on each end. The Short Duplex PCL consisted of a single 12-nucleotide oligo having a biotin on its 5' end and a photocleavable fluorescent label on its 3' end. The single biotin PCL was the same as the Standard PCL except that only one of the two oligos in each hybrid had a biotin on its 5' end. In addition, staining with an oligonucleotide having a photocleavable biotin (IDT-PCL; from Integrated DNA Technologies, Coralville, Iowa) was performed in a separate batch with an identical concentration of PCL. The IDT-PCL consisted of two 34-nucleotide oligos having a photocleavable biotin on their 5' end and a fluorescent label on their 3' end, the oligos hybridized to form a 28-nucleotide double-stranded section with four nucleotide single-stranded overhangs on each end (FIG. 12). The center of the field of view for each section was photo cleaved (3×2 sec with 2 min flush between each) during time-lapse imaging. Signal intensity was measured in two areas (ROI) of equal size: one area of specific stain and one area of background. The maximal intensity of the stain was traced over time (FIG. 10A). The difference between the signal and background was plotted both as an absolute signal (FIG. 10B) and % of maximal signal (FIG. 10C). In addition to the time-lapse capture, images of each stained section were obtained both before and after photocleavage. FIGS. 11D-H show images of each section that were produced by stitching together about 25 images. These data show that all probe variations are usable as PCLs.

Example 7

Detection of an Antigen in a Tissue Section Using PCLs with SMCC Crosslinkers

This Example illustrates an antigen-bound antigen-binding complex of formula (III). Two single stranded oligonucleotides were obtained from IDT (Integrated DNA Technologies, Coralville, Iowa) of which one oligonucleotide had a 5' C6 amino modification. The oligonucleotides were annealed to form a partially double stranded oligonucleotide and -dC-Cy5 or dU-Cy7PCLs were extended to the 3' ends. PCL synthesis was followed by RP-HPLC purification. Sulfo-SMCC (a bifunctional cross linker) was attached to the 5' amino modified strand of the duplex and the reaction was purified by RP-HPLC. Sulfo-SMCC was attached to the primary amine on the 5' end of the oligonucleotide through an amide linkage. The SMCC linker allowed direct linkage of the probe to the antibody, eliminating the need for a separate ligand-receptor connection between the probe and the antibody, such as the biotin-avidin or streptavidin linkage, described previously. Eliminating additional ligands reduced the risk of non-specific interactions and stearic hindrance.

Direct conjugation of the probe to the antibody will decrease hands-on time to complete the staining and allow for multiplex antibody staining with minimal steps and reagents. Multiple antibodies conjugated to uniquely labeled PCLs (at least up to three colors) will be premixed and used in tissue staining resulting in detection of three antigens in a single staining/imaging cycle. Three such staining cycles with a cleavage cycle at the end of each imaging event will thus result in detection of nine antigens with 70% time reduction from the previous ligand-based approach.

Other structural variations of the PCL with SMCC linker will include adding an amino modification to the oligo on the base instead of the phosphate, C12 linker in place of the C6 linker for amino modification, linking the SMCC away from the end of the oligo, and adding the SMCC linker on the same strand as incorporation rather than the opposite strand.

Direct conjugation of PCL to the SMCC linker will also be achieved through a SM(PEG)n heterobifunctional cross-linker in which a polyethylene glycol (PEG) spacer replaces the hydrocarbon-based spacer in the Sulfo-SMCC cross-linker. PEG spacer will offer more flexibility between the two functional groups, improve solubility of the reaction and final conjugate and reduce potential for aggregation of the conjugates, thus preserving functionality. Based on the size of the antibody, different lengths of the PEG linkers will be chosen to minimize the stearic hindrance of the cross linker with the PCL moiety and to maximize flexibility of the spacer arm.

Direct conjugation of PCL molecules will be synthesized by incubating heterobifunctional linkers with the amino modified oligonucleotides under suitable pH (in PBS or PBS-EDTA at pH 7-7.2), followed by clean-up using RP-HPLC and/or desalting. Subsequently, activated PCLs will be incubated with antibodies that have exposed sulfhydryl groups (reduced using 5 mM TCEP). The conjugation reaction will be further purified through a desalting column to remove unbound oligos. Alternatively, conjugation of PCL with antibodies will be achieved with the use of commercial conjugation kits that provide optimized reagents and buffers required to achieve conjugation (such as, Thunder-Link PLUS oligo conjugation system, Cat #425-000, 425-0300 offered by Innova Biosciences).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,439,356
U.S. Pat. No. 5,188,934
U.S. Patent Appl. Publ. No. 2010/0041041
PCT Publn. No. WO 2003/006625
PCT Publn. No. WO 2005/084367
PCT Publn. No. WO 2008/070749
PCT Publn. No. WO 2009/152353
PCT Publn. No. WO 2013/040257
Corrie, in *Dynamics studies in biology*, Goeldner and Givens (Eds.), Wiley-VCH Verlag GmbH & Co. KGaA, Weinheim, pp. 1-28, 2005.
Givens & Schowen, In *Chemiluminescence and Photochemical Reaction Detection in Chromatography*, J. W. Birks, Ed.; VCH: New York, pp 125-47, 1989.
Hastings, *J. Mol. Evol.* 19:309-21, 1983.
Haugland, *The Handbook; A Guide to Fluorescent Probes and Labeling Technologies*, Invitrogen, 2005.
Hermanson, Bioconjugate Techniques, $3^{rd}$ Edition, San Diego: Academic Press, 2013.
Moritz and Wahle, Simple methods for the 3' biotinylation of RNA, RNA, 20:421-427, 2014.
Nieman, In *Chemiluminescence and Photochemical Reaction Detection in Chromatography*, J. W. Birks, Ed.; VCH: New York, pp 99-123, 1989.
Orosz et al., *Crit. Rev. Anal. Chem.*, 26:1-27, 1996.
Proudnikov and Mirzabekov, Chemical methods of DNA and RNA fluorescent labeling, Nuc. Acids Res., 24:4535-4532, 1996.
Riedel et al., Labelling of nucleosides and oligonucleotides by solvatochromic 4-aminophthalimide fluorophore for studying DNA-protein interactions, Chem. Sci, 3:2797-2806, 2012.
Seo et al., *Proc. Natl. Acad. Sci. USA*, 102:5926-5931, 2005.

What is claimed is:

1. A method for detecting the presence of an at least first antigen on or in a sample comprising a first antigen-binding complex capable of specifically binding the at least first antigen, the method comprising detecting the presence of a photocleavable label in the sample, wherein the photocleavable label is conjugated to the first antigen-binding complex through a functional linker, wherein the first antigen-binding complex is non-covalently bound to the at least first antigen forming an antigen-bound antigen-binding complex of formula (I):

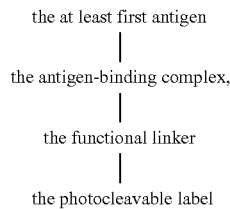

wherein the presence of the photocleavable label is indicative of the presence of the at least first antigen; wherein the functional linker is an at least partially double-stranded oligonucleotide, wherein each oligonucleotide of the at least partially double-stranded oligonucleotide is 34 nucleotides in length and wherein the at least partially double-stranded oligonucleotide has a double-stranded section that is 28 nucleotides in length, wherein each oligonucleotide in the at least partially double-stranded oligonucleotide has a biotin on its 5' end.

2. The method of claim 1, further comprising photocleaving the photocleavable label.

3. The method of claim 2, wherein photocleaving comprises exposing the sample to ultraviolet light.

4. The method of claim 1, wherein the photocleavable label comprises a reporter moiety covalently bound to a photocleavable moiety.

5. The method of claim 4, wherein the photocleavable moiety is selected from the group consisting of a 2-nitrobenzyl group, a benzoin group, a coumarinyl group, and a p-hydroxyphenacyl group.

6. The method of claim 5, wherein the photocleavable moiety is a 2-nitrobenzyl group.

7. The method of claim 6, wherein the 2-nitrobenzyl group comprises a substitution on the α-carbon and/or a 5-methoxy substitution on the benzene ring.

8. The method of claim 4, wherein the reporter moiety is a colorimetric dye, a fluorescent dye, a radioactive label, a chemiluminescent group, or a bioluminescent group.

9. The method of claim 1, wherein the sample is a tissue section, biopsy sample, cell culture sample, cell smear, or protein lysate.

10. The method of claim 1, wherein each oligonucleotide in the at least partially double-stranded oligonucleotide has a photocleavable label on its 3' end.

11. The method of claim 1, wherein the first antigen-binding complex is defined by formula (II):

a primary antibody
|
a conjugation moiety, wherein the first antigen-binding complex comprises a primary antibody bound to a conjugation moiety, wherein the antigen-bound antigen-binding complex is further defined by formula (III):

the at least first antigen
|
the primary antibody
|
the conjugation moiety
|
the functional linker
|
the photocleavable label.

12. The method of claim 11, wherein the primary antibody is modified by at least one reducing agent.

13. The method of claim 11, wherein the conjugation moiety is a heterobifunctional linker.

14. The method of claim 1, wherein the first antigen-binding complex is defined by formula (IV):

a primary antibody,
|
a first ligand
|
a first anti-ligand wherein the first antigen-binding complex comprises a primary antibody covalently bound to a first ligand, wherein the first ligand is non-covalently bound to a first anti-ligand, wherein the antigen-bound antigen-binding complex is further defined by formula (V):

the at least first antigen
|
the primary antibody
|
the first ligand
|
the first anti-ligand
|
the functional linker
|
the photocleavable label.

15. The method of claim 1, wherein the first antigen-binding complex is defined by formula (VI):

a primary antibody,
|
a first ligand
|
a first anti-ligand
|
a second ligand wherein the first antigen-binding complex comprises a primary antibody covalently bound to a first ligand, wherein the first ligand is non-covalently bound to a first anti-ligand, wherein the second ligand is non-covalently bound to the first anti-ligand, wherein the antigen-bound antigen-binding complex is further defined by formula (VII):

the at least first antigen
|
the primary antibody
|
the first ligand
|
the first anti-ligand
|
the second ligand
|
the functional linker
|
the photocleavable label.

16. The method of claim 1, wherein the first antigen-binding complex is defined by formula (VIII):

a primary antibody,
|
a secondary ligand
|
a first ligand
|
a first anti-ligand wherein the first antigen-binding complex comprises a primary antibody bound by a secondary antibody, wherein the secondary antibody is covalently bound to a first ligand, wherein the first ligand is non-covalently bound to a first anti-ligand, wherein the antigen-bound antigen-binding complex is further defined by formula (IX):

the at least first antigen
|
the primary antibody
|
the secondary antibody
|
the first ligand
|
the first anti-ligand
|
the functional linker
|
the photocleavable label.

17. The method of claim 1, wherein the first antigen-binding complex is defined by formula (X):

a primary antibody
|
a secondary antibody,
|
a first ligand
|
a first anti-ligand
|
a second ligand wherein the first antigen-binding complex comprises a primary antibody bound by a secondary antibody, wherein the secondary antibody is covalently bound to a first ligand, wherein the first ligand is non-covalently bound to a first anti-ligand, wherein the second ligand is non-covalently bound to the first anti-ligand, wherein the antigen-bound antigen-binding complex is further defined by formula (XI):

the at least first antigen
|
the primary antibody
|
the secondary antibody
|
the first ligand
|
the first anti-ligand
|
the second ligand
|
the functional linker
|
the photocleavable label.

* * * * *